United States Patent
Cheng et al.

(10) Patent No.: US 10,421,783 B2
(45) Date of Patent: Sep. 24, 2019

(54) PROSTATE-SPECIFIC MEMBRANE ANTIGEN (PSMA) TARGETING PEPTIDES

(71) Applicants: Kun Cheng, Kansas City, MO (US); Wei Jin, Kansas City, MO (US)

(72) Inventors: Kun Cheng, Kansas City, MO (US); Wei Jin, Kansas City, MO (US)

(73) Assignee: The Curators of the University of Missouri, Columbia, MO (US)

( * ) Notice: Subject to any disclaimer, the term of this patent is extended or adjusted under 35 U.S.C. 154(b) by 0 days.

(21) Appl. No.: 15/437,248

(22) Filed: Feb. 20, 2017

(65) Prior Publication Data

US 2017/0240596 A1    Aug. 24, 2017

Related U.S. Application Data

(60) Provisional application No. 62/297,593, filed on Feb. 19, 2016.

(51) Int. Cl.
| | | |
|---|---|---|
| *A61K 38/00* | (2006.01) | |
| *C07K 7/08* | (2006.01) | |
| *A61K 38/10* | (2006.01) | |
| *A61K 49/00* | (2006.01) | |
| *G01N 33/574* | (2006.01) | |

(52) U.S. Cl.
CPC ............... *C07K 7/08* (2013.01); *A61K 38/10* (2013.01); *A61K 49/00* (2013.01); *A61K 49/0043* (2013.01); *A61K 49/0052* (2013.01); *G01N 33/57434* (2013.01); *G01N 33/57492* (2013.01); *A61K 38/00* (2013.01); *C07K 2319/035* (2013.01); *C07K 2319/33* (2013.01)

(58) Field of Classification Search
CPC .................................................... A61K 38/00
See application file for complete search history.

(56) References Cited

PUBLICATIONS

Shen et al. (PLoS One. Jul. 25, 2013; 8 (7): e68339; pp. 1-8).*
Qin et al. (Pharm. Res. Oct. 2011; 28 (10): 2422-34; author manuscript; pp. 1-21).*
Ronnanov et al. (Prostate. Jun. 1, 2001; 47 (4): 239-51).*
Banerjee et al. (Oncotarget. Dec. 2011; 2 (12): 1244-53).*
Schmittgen et al. (Int. J. Cancer. Nov. 1, 2003; 107 (2): 323-9).*
Moktan et al. (Int. J. Pept. Res. Ther. Sep. 2012; 18 (3): 227-237; author manuscript, pp. 1-18).*
Jin, et al., Discovery of PSMA-specific Peptide Ligands for Targeted Drug Delivery, International Journal of Pharmaceutics, 2016, pp. 138-147, Elsevier.
Chen et al., Discovery of Peptide Ligands for Hepatic Stellate Cells Using Phage Display, Mol Pharm., 2015, pp. 1-22, 12(6): 2180-2188.
Giordano, et al., Biopanning and Rapid Analysis of Selective Interactive Ligands, Nat. Med., 2001, pp. 1-2, 7(11): 1249-53.
Javadpour, et al., De novo Antimicrobial Peptides With Low Mammalian Cell Toxicity, J Med Chem., 1996, pp. 1-2, 39 (16): 3107-13.
Jia, et al., Coexpression of Vascular Endothelial Growth Factor and Interleukin-1 Receptor Antagonist for Improved Human Islet Survival and Function, Mol. Pharm., 2007, pp. 1-2, 4(2): 199-207.
Barve et al., Prostate Cancer Relevant Antigens and Enzymes for Targeted Drug Delivery, PubMed Journals, 2014, pp. 1-4.
Mai, et al., A Proapoptotic Peptide for the Treatment of Solid Tumors, Cancer Res., 2001, pp. 1, 61(21): 7709-12.
McNamara, et al., Cell Type-specific Delivery of siRNAs with Aptamer-siRNA Chimeras, Nat. Biotechnol., 2006, pp. 1-2, 24(8): 1005-15.
Qin, et al., Identification of a LNCaP-Specific Binding Peptide Using Phage Display, Pharm Res., 2011, pp. 1-21, 28 (10): 2422-2434.

* cited by examiner

*Primary Examiner* — Stephen L Rawlings
(74) *Attorney, Agent, or Firm* — Bassam S. Nader; Brannon Sowers & Cracraft PC

(57) ABSTRACT

Described herein is the discovery of novel PSMA-specific peptides, which were identified through a novel combinatorial biopanning method. One of the novel PSMA-specific peptides discovered, GTIQPYPFSWGY (or GTI) (SEQ ID NO: 2), exhibits high binding affinity and selectivity to PSMA and PSMA-positive prostate cancer cells. It was found that GTI can mediate internalization of the apoptotic KLA peptide (SEQ ID NO: 10) to PSMA-positive LNCaP cells and induce cell death. Moreover, a FAM-labeled GTI peptide shows a high and specific tumor uptake in nude mice bearing human prostate cancer xenografts. It was demonstrated that the GTI peptide can be employed as a PSMA-specific ligand for prostate cancer diagnosis and/or for targeted drug delivery to prostate cancer cells.

12 Claims, 16 Drawing Sheets

Specification includes a Sequence Listing.

| Pep. | $K_d$ LNCaP (μM) |
|---|---|
| NRP | 30.69 |
| SMA | >100 |
| YPT | >100 |
| QPG | 23.62 |

| Pep. | $K_d$ (μM) | |
|---|---|---|
| | LNCaP | C4-2 |
| GTI | 8.22 | 8.91 |
| TGH | 8.01 | 44.05 |
| HSD | 12.80 | 30.77 |
| YVN | 9.34 | 9.79 |

FIG. 5D

PROSTATE-SPECIFIC MEMBRANE ANTIGEN (PSMA) TARGETING PEPTIDES

CROSS-REFERENCE TO RELATED APPLICATIONS

This application claims priority under 35 USC § 119(e) to U.S. Provisional Application Ser. No. 62/297,593, filed on Feb. 19, 2016, the entire disclosure of which is incorporated herein by reference.

GOVERNMENT RIGHTS

This invention was made with Government support under Grant No. 1R01AA021510 awarded by the National Institutes of Health. The U.S. government has certain rights in the invention.

SEQUENCE LISTING

The instant application contains a Sequence Listing which has been submitted electronically in ASCII format and is hereby incorporated by reference in its entirety. Said ASCII copy, created on Apr. 28, 2017, is named 745-13517_SL.txt and is 6,036 bytes in size.

TECHNICAL FIELD

The present invention relates to tissue specific anti-cancer therapeutic compositions, to a novel method for identifying said compositions, and to methods of use of said compositions in diagnosing and treatment of cancer.

BACKGROUND AND SUMMARY OF THE INVENTION

Prostate cancer is the most commonly diagnosed malignancy and second-most prevalent cause of cancer death in American men. The estimated death of prostate cancer in 2015 was 27,540, which accounted for about 9% of all male cancer deaths in the United States. Conventional therapies for prostate cancer include surgery, radiation, and hormone therapy. Although these treatments are relatively efficient for early stage prostate cancer, it is known that most patients with localized prostate cancer ultimately relapse. Chemotherapy is currently widely used for advanced prostate cancer treatment, but with limited success. Lack of targeted delivery, partly because of the lack of agents that possess tissue specificity, is one of the major hurdles that limit the effectiveness of cancer chemotherapy. Thus, a great deal of attention has been paid to the development of targeted drug delivery systems for prostate cancer therapy.

Prostate-specific membrane antigen (PSMA), also known as NAAG peptidase, glutamate carboxypeptidase II (GC-PII), or N-acetyl-L-aspartyl-L-glutamate peptidase I (NAALADase I), is a transmembrane glycoprotein that in humans is encoded by the FOLH1 (folate hydrolase 1) gene. Human PSMA contains 750 amino acids, including a large extracellular domain (707 amino acids), an intracellular domain (19 amino acids), and a transmembrane domain (24 amino acids). It weighs approximately 100 kDa. It is an enzyme that is a type II transmembrane glycosylated protein with folate hydrolase activity, and is known to be overexpressed not only in nearly all prostate cancer cells but also in tumor neovasculature of a variety of cancers (see: Wright Jr., G. L., et al., Urol. Oncol., 1995, 1(1):18-28; Chang, S. S., et al., Clin. Cancer Res., 1999, 5(10):2674-2681; O'Keefe, D. S., et al., Biochim. Biophys. Acta, 1998, 1443 (1-2):113-127). By contrast, its expression in normal prostate epithelium tissues and other normal tissues has been reported to be 100-1000 fold lower (see: Wright Jr., G. L., et al., Urol. Oncol., 1995, 1(1):18-28; and others). Moreover, the expression level of PSMA correlates with prostate cancer progression. PSMA, therefore, is a validated target for prostate cancer therapy and has been adopted as a biomarker for diagnosis and imaging, and as a targeting receptor for prostate cancer therapy because of its overexpression in most prostate cancer cells. Aptamers and antibodies targeting PSMA have been discovered for targeted drug delivery to prostate cancer cells in the past few years (see: Barve, A., et al., J. Control. Release, 2014, 187:118-132). Although aptamers and antibodies retain high binding affinity to PSMA, their drawbacks, such as large size, possible immunogenicity and instability, may limit their applications in targeted drug delivery. In contrast, peptides are believed to have several advantages, including a small molecular weight, high permeability, great stability, less immunogenicity, ease of synthesis, and flexibility in chemical conjugation. Moreover, it has been reported that peptides can achieve high binding affinity and specificity that are comparable with antibodies (see: Pazgier, M., et al., Proc. Natl. Acad. Sci. U.S.A, 2009, 106(12):4665-4670; Huang, L., et al., J. Biol. Chem., 2003, 278(18): 15532-15540).

As a carboxyl peptidase, it has been reported that PSMA can cleave the terminal glutamate from NAAG or γ-linked polyglutamate. It was also reported that the enzymatic activity of PSMA was found elevated in prostate cancer cells, indicating its important role in prostate cancer progression by regulating angiogenesis. Therefore, it has been suggested that inhibition of the PSMA enzymatic activity could be a potential therapeutic approach for prostate cancer. Aggarwal and colleagues identified the peptide WQPDTAH-HWATL (SEQ ID NO: 1), which can specifically bind to the catalytic site of PSMA and inhibit its enzymatic activity with an $IC_{50}$ of 23 µM (Aggarwal, S., et al., Cancer Res., 2006, 66(18):9171-9177). However, it has been found that the GTIQPYPFSWGY (GTI) peptide (SEQ ID NO: 2) disclosed herein (see below) does not inhibit the PSMA enzymatic activity, which may be taken as indicating that the GTI peptide binds to a different site of PSMA extracellular domain (ECD) rather than the catalytic site.

Phage display has been widely used to identify peptide ligands for a wide variety of molecular targets, including proteins and various molecular moieties, cells, or animal tissues. A phage display library contains billions of different phages, and each phage retains a unique inserted peptide sequence on the surface. Phage display technology therefore provides a high-throughput tool for affinity selection. Protein-based biopanning and cell-based biopanning are the two most common strategies to identify peptide ligands, but both of them have disadvantages when they are used alone (see: Chen, Z., et al., Mol. Pharm., 2015, 12(6):2180-2188; Qin, B., et al., Pharm. Res., 2011, 28(10):2422-2434).

Binding affinity of peptide ligands to their receptor is known to be generally lower compared to antibodies. However, there are several strategies to increase the binding affinity of phage derived peptides. For example, affinity maturation is often employed to improve the binding affinity of peptide ligands by mutagenesis. After additional rounds of selection with these affinity maturation libraries, peptide ligands with higher affinity can be discovered. In addition, dimerization or tetramerization is a common approach to improve the binding affinity of peptides. For instance, it has been recently demonstrated that dimerization of an IGF2R- specific peptide improves its apparent affinity by nearly 9-fold (see: Chen, Z., et al., *Mol. Pharm.,* 2015, 12(6):2180-2188). Modification of peptide side-chains and substitution of D-amino acids are other reported strategies to improve binding affinity. For example, Chen and colleagues replaced glycines with D-form amino acids and significantly improved the binding affinity and stability of the peptide (see: Chen, S., et al., *Chembiochem,* 2013, 14(11):1316-1322).

Most biopannings so far are conducted on a single target, such as a recombinant protein, a cell line, or a tissue. However, each of these methods has its own advantages and disadvantages. For example, a recombinant protein may exhibit a different conformation structure from its native form in cells. Therefore, a peptide ligand discovered by biopanning on recombinant protein may not exhibit the same affinity to its target cells in vitro and in vivo. On the other hand, the intricate and complex structures of cell membranes may lead to the discovery of a peptide ligand that binds to an unknown moiety. A recently conducted whole cell biopanning on PSMA-positive LNCaP cells identified a peptide ligand that exhibits very high affinity and specificity to LNCaP cells; however, this peptide was not PSMA-specific and its target moiety is unknown (Qin, B., et al., *Pharm. Res.,* 2011, 28(10):2422-2434). Subsequently, future clinical application of this type of peptide ligands may be unpredictable. In addition, peptide ligands identified from in vitro biopanning may not survive the complex environment in the body after systemic administration.

In one embodiment of the invention, provided herein is a novel method for identifying PSMA-specific peptides that may be useful in vivo for prostate cancer diagnosis and therapy. In one aspect, said method includes a step of combinatorial biopanning against recombinant human PSMA extracellular domain (ECD), PSMA-positive LNCaP cells, and LNCaP xenografts in nude mice. Details of said novel method are provided below. A related embodiment of the invention herein provides novel peptides identified by using said method, which exhibit high affinity and specificity to PSMA in vitro and in vivo. One particular peptide identified is GTIQPYPFSWGY (or GTI) (SEQ ID NO: 2), which shows high affinity and specificity to PSMA in vitro and in vivo, and exhibits significantly higher uptake in tumor tissue than uptake in other tissues, including liver, kidneys, muscle, heart, lungs, and spleen. In another embodiment, it is demonstrated herein that said GTI peptide can be used in diagnosis of cancer by virtue of its ability to localize on cancer cells, such as PSMA-positive prostate cancer cells. Thus, said GTI peptide is capable of delivering attached imaging agents to the cancer cells. Illustratively, said GTI peptide was used as described herein to deliver an attached fluorescence agent to PSMA-positive prostate cancer cells. In another embodiment, it is demonstrated herein that said GTI peptide can be used in therapy of cancer cells, such as PSMA-positive prostate cancer cells, by delivering attached therapeutic cargos to the cancer cells. Illustratively, said GTI peptide was used as described herein to deliver a fused proapoptotic peptide, known to be incapable of entering the cells on its own, to PSMA-positive prostate cancer cells, resulting in cytotoxicity to the cancer cells. This demonstrates that said GTI peptide mediates internalization of the proapoptotic peptide into the cells.

Another embodiment of the invention herein provides a novel combinatorial phage biopanning procedure developed to discover PSMA-specific peptides that can potentially be used as ligands for targeted drug delivery to prostate cancer cells. This procedure includes conducting multiple rounds of biopanning against recombinant human PSMA extracellular domain (ECD), PSMA-positive LNCaP cells, and LNCaP xenografts in nude mice. In one illustrative example, five rounds of biopanning against recombinant human PSMA extracellular domain (ECD), PSMA-positive LNCaP cells, and LNCaP xenografts in nude mice were conducted, and various affinity assays were carried out to identify high-affinity peptides for PSMA ECD and PSMA-positive prostate cancer cells. Among these high affinity peptides, the GTI peptide disclosed herein shows the highest affinity as well as specificity to PSMA in prostate cancer cells. The apparent $K_d$ values of the GTI peptide to PSMA-positive LNCaP and C4-2 cells are 8.22 μM and 8.91 μM, respectively. It is disclosed herein that the GTI peptide can specifically deliver the proapoptotic peptides to the prostate cancer cells to induce cell death. One such proapoptotic peptide, $_D$(KLAK-LAK)$_2$, fused to the GTI peptide, is successfully delivered to LNCaP cells, inducing cell death. In a biodistribution study, the GTI peptide disclosed herein shows the highest uptake in C4-2 xenografts, while its uptake in other major organs, such as the liver and spleen, are either low or negligible. Compared to its scrambled control (random permutation of the GTI peptide), the GTI peptide exhibits higher and more specific uptake in C4-2 xenografts. All the results disclosed herein indicate that the GTI peptide is a potentially promising ligand for PSMA-targeted drug delivery for prostate cancer therapy.

BRIEF DESCRIPTION OF THE DRAWINGS

FIG. 5D displays the apparent equilibrium dissociation constants ($K_d$) of the selected peptides in LNCaP and C4-2 cells.

DETAILED DESCRIPTION

Figure 1:
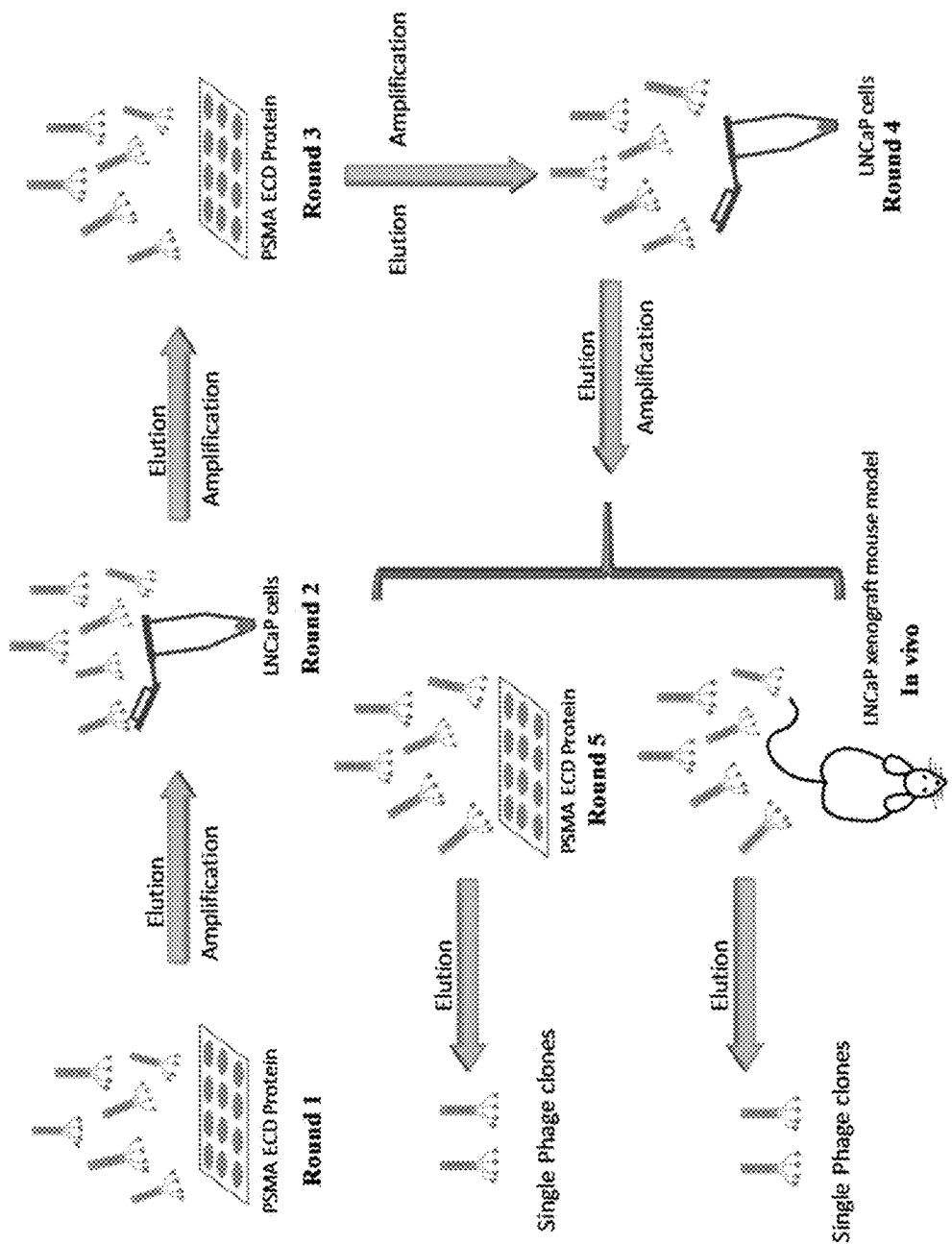
FIG. 1 is a scheme showing the combinatorial phage biopanning of the invention, which was conducted against recombinant human PSMA extracellular domain (ECD), PSMA-positive LNCaP cells, and LNCaP xenografts in nude mice.

Before the present methods, implementations and systems are disclosed and described, it is to be understood that this invention is not limited to specific components, specific methods, specific implementation, or to particular compositions, and as such may, of course, vary. It is also to be understood that the terminology used herein is for the purpose of describing particular implementations only and is not intended to be limiting. Neither are mechanisms which have been provided to assist in understanding the disclosure meant to be limiting.

One embodiment of the invention provides a novel method that is useful for identifying peptides that exhibit high affinity and specificity to cancer cells, in vitro and in vivo, particularly to PSMA-positive prostate cancer cells. This method is represented schematically in FIG. 1, and is described in detail in the Examples section. This method comprises peptide screening steps, including the use of a combinatorial phage biopanning technique. Illustratively, in the case of PSMA, the novel method comprises the steps of: (a) carrying out combinatorial phage biopanning in vitro and in vivo in multiple rounds against recombinant human PSMA extracellular domain, PSMA-positive LNCaP cells, and LNCaP xenograft tumors; (b) randomly selecting and amplifying a set of individual phage clones from the combinatorial phage biopanning step; (c) determining the binding affinities of the selected phage clones in PSMA-positive LNCaP and PC-3 cells using cell phage ELISA; (d) selecting the phage clones with higher affinity for PSMA-positive LNCaP cells; and, (e) sequencing the phage clones selected in the previous step to identify the peptides expressed by these phage clones. Additionally, the method may further comprise the steps of: (a) selecting the phage clones that encode the identified peptides that were found in both in vitro and in vivo biopannings; (b) pre-incubating LNCaP cells with the encoding peptides, followed by washing, and by incubating with the corresponding phages; and, (c) identifying the peptides that show the highest competitive inhibition relative to their corresponding phages. Accordingly, by using the identification method described above and in the Examples section, several PSMA-specific peptide compositions that show high affinity and specificity to PSMA extracellular domain (ECD) and PSMA-positive prostate cancer cells, in both in vitro and in vivo assays, were identified, including:

| | |
|---|---|
| GTIQPYPFSWGY, | (SEQ ID NO: 2) |
| SMAGEQISWALI, | (SEQ ID NO: 3) |
| NRPDSAQFWLHH, | (SEQ ID NO: 4) |
| QPGHAILAQHPT, | (SEQ ID NO: 5) |
| YVNSHSILGYTG, | (SEQ ID NO: 6) |
| TGHLYPTRMEIQ, | (SEQ ID NO: 7) |
| HSDNHYRPADKL, | (SEQ ID NO: 8) |

-continued and

YPTDWLWHGHNK. (SEQ ID NO: 9)

Another embodiment of the invention provides PSMA-specific peptide compositions identified by use of the novel method described herein. These PSMA-specific peptide compositions show high affinity and specificity to PSMA extracellular domain (ECD) and PSMA-positive prostate cancer cells, in both in vitro and in vivo assays. Additionally, it was discovered that these PSMA-specific peptide compositions do not inhibit PSMA enzymatic activity. Without being bound by theory, this discovery may be taken as indicating that the PSMA-specific peptide compositions of the invention bind at a different site of the PSMA extracellular domain rather than the catalytic site. In one aspect, the PSMA-positive prostate cancer cells, towards which the peptide compositions of the invention exhibit high affinity and specificity, include the cancer cells known as LNCaP cells, C4-2 cells, and CWR22Rv1 cells, but may also include other similar cancer cells as well. Illustrative of the PSMA-specific peptide compositions of the invention are the following peptides, identified by the above method: GTIQPYPFSWGY (SEQ ID NO: 2), SMAGEQISWALI (SEQ ID NO: 3), NRPDSAQFWLHH (SEQ ID NO: 4), QPGHAILAQHPT (SEQ ID NO: 5), YVNSHSILGYTG (SEQ ID NO: 6), TGHLYPTRMEIQ (SEQ ID NO: 7), HSDNHYRPADKL (SEQ ID NO: 8), and YPTDWLWHGHNK (SEQ ID NO: 9). In particular, the PSMA-specific peptide GTIQPYPFSWGY (or GTI for short) (SEQ ID NO: 2) identified herein shows very high affinity and specificity towards PSMA-positive prostate cancer cells. In one key aspect of the invention, the PSMA-specific peptide compositions herein show significantly higher uptake in tumor tissue than in other tissues, including the liver, kidneys, muscle, heart, lungs, and spleen. For example, the PSMA-specific peptide GTI exhibited an uptake ratio in tumor tissue relative to muscle tissue of at least 3:1. This discovery of a higher uptake of the PSMA-specific peptide compositions into tumor tissue relative to other tissues is very interesting, because it is well known that the kidneys and liver are the major sites of peptide metabolism. Stated another way, this means that the affinity of the PSMA-specific peptide compositions, such as GTI, to the kidneys and liver is much lower than their affinity to tumor tissue.

In another embodiment, provided herein is a diagnostic composition for cancer imaging. This diagnostic composition comprises one or more of the PSMA-specific peptide compositions identified by the method described herein and one or more imaging agents. The one or more PSMA-specific peptide compositions and the one or more imaging agents are fused (or attached) together using any of the fusing (or attaching) techniques known in the art, such as via covalent bonding, ionic bonding, and the like, to form a diagnostic composition having a peptide portion with PSMA-specificity and affinity and an imaging moiety. A preferred embodiment of the invention is a diagnostic composition formed by fusing together GTI with an imaging agent. Any of the common imaging agents known in the art may be used, such as any of the known fluorescing agents. Illustratively, demonstrated in the examples herein is a diagnostic composition formed by combining GTI and fluorescein amidite (commonly known as FAM) to form a FAM-labeled GTI diagnostic composition.

In another embodiment, provided herein is a method of diagnosing cancer, such as prostate cancer, in a patient, said method utilizing the diagnostic composition described above. A related embodiment provides a method of use of the diagnostic composition described above to diagnose cancer, such as prostate cancer, in a patient. Thus, either method comprises the step of administering an effective amount of the diagnostic composition to the patient, allowing sufficient time for the diagnostic composition to localize on any cancer cells, such as prostate cancer cells, and then using an imaging technique to determine the presence or absence of cancer cells. Illustratively, the FAM-labeled GTI diagnostic composition described above may be used. As contemplated herein, any suitable imaging technique known in the art may be used. Also, as contemplated herein, the cancer diagnostic method herein may be used in conjunction with other cancer diagnostic methods known in the art.

In another embodiment, provided herein are ligands for targeted drug delivery to cancer cells, such as prostate cancer cells. Said ligands comprise a peptide that shows high affinity and specificity to cancer cells. In a preferred embodiment, the ligands comprise a PSMA-specific peptide that shows high affinity and specificity to PSMA extracellular domain and PSMA-positive prostate cancer cells in vitro and in vivo. In one aspect of the preferred embodiment, the peptide does not inhibit PSMA enzymatic activity. Illustrative of the PSMA-positive prostate cancer cells are LNCaP cells, C4-2 cells, or CWR22Rv1 cells, and the like. In another important aspect, the peptide comprised in the ligands shows higher uptake in tumor tissue than in other tissues including the liver, kidneys, muscle, heart, lungs, and spleen. For example, the uptake ratio of the peptide in tumor tissue relative to muscle tissue is at least 3:1. Illustrative of the peptides comprised in the ligands are the following peptides, identified by the above biopanning method: GTIQPYPFSWGY (GTI) (SEQ ID NO: 2), SMAGEQISWALI (SEQ ID NO: 3), NRPDSAQFWLHH (SEQ ID NO: 4), QPGHAILAQHPT (SEQ ID NO: 5), YVNSHSILGYTG (SEQ ID NO: 6), TGHLYPTRMEIQ (SEQ ID NO: 7), HSDNHYRPADKL (SEQ ID NO: 8), and YPTDWLWHGHNK (SEQ ID NO: 9). In a preferred embodiment, the peptide comprised in the ligands is GTI.

In another embodiment, provided herein is a therapeutic composition for treating cancer. This therapeutic composition comprises a PSMA-specific peptide identified via the identification method described above and a biologically active moiety, wherein the PSMA-specific peptide and the biologically active moiety are fused (or attached) to each other. The fusing (or attaching) may be accomplished via any of the techniques known in the art, and may be covalent bonding, ionic bonding, and the like. This provides a therapeutic composition having a peptide portion with PSMA-specificity and affinity and a biologically active moiety. Illustratively, the PSMA-specific peptide may be any one of GTIQPYPFSWGY (GTI) (SEQ ID NO: 2), SMAGEQISWALI (SEQ ID NO: 3), NRPDSAQFWLHH (SEQ ID NO: 4), QPGHAILAQHPT (SEQ ID NO: 5), YVNSHSILGYTG (SEQ ID NO: 6), TGHLYPTRMEIQ (SEQ ID NO: 7), HSDNHYRPADKL (SEQ ID NO: 8), and YPTDWLWHGHNK (SEQ ID NO: 9). In a preferred embodiment, the PSMA-specific peptide is GTI. The biologically active moiety can be any cytotoxic moiety. In one illustrative example, the biologically active moiety can be a proapoptotic moiety. For example, the proapoptotic moiety can be one that is derived by attaching the antimicrobial peptide KLAKLAKKLAKLAK (SEQ ID NO: 10) to the PSMA-specific peptide. In a second illustrative example, the biologically active moiety can be an anticancer moiety derived by attaching an anti-cancer drug to the PSMA-specific peptide. As contemplated herein, any anti-cancer drug known in the art may be used.

Another embodiment of the invention provides a method of use of the therapeutic composition described above for treating a patient suffering from cancer. In a preferred embodiment, it is used for treating a patient suffering from prostate cancer. This method of use comprises the step of administering to the patient a therapeutically effective amount of the therapeutic composition, which therapeutic composition comprises a PSMA-specific peptide, e.g., GTI, and a biologically active moiety, as described herein. Alternatively, the method comprises the step of administering to the patient a therapeutically effective amount of a pharmaceutically or medicinally acceptable formulation or preparation that includes the therapeutic composition of the invention. As contemplated herein, any of the pharmaceutically or medicinally acceptable formulations or preparations known in the art may be used. Also, as contemplated herein, the method of use of the therapeutic composition herein may include co-administration with one or more other drugs, compositions, and/or formulations, including other anti-cancer or chemotherapeutic drugs. Likewise, the method may include, or be combined with, the use of any other co-therapies, such as, illustratively, radiation therapy, and the like.

While the novel technology herein has been illustrated and described in detail in the foregoing description, and in the following examples and the figures herein, the same is to be considered as illustrative and not restrictive in character. It is understood that one of ordinary skill in the art could readily make a nigh-infinite number of insubstantial changes and modifications to the above-described embodiments and that it would be impractical to attempt to describe all such embodiment variations in the present specification. Accordingly, it is understood that all changes and modifications that come within the spirit of the novel technology are desired to be protected.

EXAMPLES

The following examples further illustrate specific embodiments of the invention. However, the following examples should not be interpreted in any way to limit the invention.

Example 1

Materials. The Ph.D.™-12 phage display peptide library and *E. coli* ER2738 were purchased from New England Biolabs (Beverly, Mass.). LNCaP, PC-3, C4-2, CWR22Rv1, and HeLa cells were obtained from American Type Culture Collection (Manassas, Va.). HSC-T6 cell line was kindly provided by Dr. Scott L. Friedman from New York University. $_D$(KLAKLAK)$_2$ peptide was purchased from Anaspec, Inc (Fremont, Calif.). All other peptides including FAM-labeled peptides and GTI-KLA fusion peptides were purchased from United Biosystems Inc (Herndon, Va.). Non-enzymatic cell dissociation solution was obtained from MP Biomedicals (Santa Ana, Calif.). Homozygous nude mice were ordered from The Jackson Laboratory (Bar Harbor, Me.).

Example 2

Cell culture. LNCaP, C4-2, CWR22Rv1 and PC-3 cells were maintained in RPMI-1640 medium with 10% FBS, 100 U/mL penicillin and 100 μg/mL streptomycin. HSC-T6 and HeLa cells were cultured in DMEM medium with 10% FBS and penicillin/streptomycin. The cells were incubated in a 5% $CO_2$-humidified atmosphere incubator at 37° C. and passaged when they reached 80% confluence.

Example 3

Cloning and expression of PSMA ECD. The plasmid pcDNA3.1-PSMA encoding full-length human PSMA was provided by Dr. Shawn E. Lupold (Johns Hopkins University School of Medicine, Baltimore, Md.). PSMA ECD was amplified from the plasmid using the forward primer 5'-ATCAGATCTAAATCCTCCAATGAAGC-3' (SEQ ID NO: 11) and reverse primer 5'-ATCAAGCTTCTGCACT-GTGAAGGCTGCAACATA-3' (SEQ ID NO: 12). The amplified fragment was excised using BglII and HindIII, purified using a PCR Clean-Up kit, and cloned into the pRSET A vector (Invitrogen, Grand Island, N.Y.) as published (Jia, X., et al., *Mol. Pharm.*, 2007, 4(2):199-207). The pRSET A vector encoding PSMA ECD was transformed into BL21 (DE3)pLysS competent cells. The transformed competent cells were cultured in LB medium, and IPTG was added to induce the expression of PSMA ECD when the OD600 reached 0.5. After four hours of induction, the cells were harvested, lysed, and the expressed protein was collected.

Example 4

Combinatorial phage biopanning against the recombinant human PSMA ECD, LNCaP cells, and xenograft LNCaP tumor. As seen in FIG. 1, a combinatorial phage biopanning procedure was conducted against recombinant human PSMA ECD (the first, third, and fifth rounds), LNCaP cells (the second and fourth rounds), and xenograft LNCaP tumor (the fifth round). Biopanning against recombinant protein was conducted as was published before (Chen, Z., et al., *Mol. Pharm.*, 2015, 12(6):2180-2188). Briefly, ten micrograms of the recombinant human PSMA ECD was coated on 24-well plates at 4° C. overnight. Ten microliters of the M13 phage display library ($10^{13}$ pfu/mL) were incubated with PSMA ECD at 4° C. for one hour under gentle shaking. Unbound phages were removed by washing the immobilized PSMA ECD with PBST (0.1% Tween 20) three times. Bound phages were eluted by adding 0.2 M glycine-HCl (pH 2.2) and amplified by infecting ER2738 bacteria.

Biopanning against LNCaP cells was conducted as reported (Qin, B., et al., *Pharm. Res.*, 2011, 28(10):2422-2434; Giordano, R. J., et al., *Nat. Med.*, 2001, 7(11):1249-1253). Briefly, PC-3 and LNCaP cells were harvested with ice cold PBS containing 5 mM EDTA and suspended in RPMI-1640 medium at a density of $1 \times 10^7$ cells/mL. Phages from the previous round ($10^{11}$ pfu) were incubated with PC-3 cells (PSMA negative) at 4° C. for one hour to remove non-specific bound phages. The precleaned phages were incubated with LNCaP cells (PSMA positive) at 4° C. for one hour under gentle rotation. The cell suspension was then mixed with 200 μL of an organic phase composed of dibutyl phthalate and cyclohexane (9:1, v/v). After centrifugation at 10,000 RPM for 10 min, the mixture was snap frozen using liquid nitrogen. The bottom of the tube was sliced off, and bound phages in the cell pellet were recovered by infecting ER2738 bacteria.

Part of the phages from the fourth round was used for an additional biopanning against recombinant PSMA ECD, while the other part was used for in vivo biopanning against xenograft LNCaP tumor. The animal experiment was conducted under a protocol approved by the University of Missouri-Kansas City Institutional Animal Care and Use Administrative Advisory Committee. Male nude mice aged 5-6 weeks were subcutaneously inoculated with LNCaP cells to generate prostate cancer xenografts. Once the tumor volume reached 1 cm$^3$, 2×10$^9$ pfu of the fourth round phages were injected into the nude mouse via tail vein. After one hour, the nude mouse was sacrificed and the heart was perfused with 50 mL PBS to remove unbound phages in the body. The xenograft tumors were harvested and homogenized in TBS buffer. After centrifugation to remove the supernatant, the cell pellet was washed three times with TBS buffer (pH 7.4), followed by the addition of 0.2 M glycine HCl (pH 2.2) to adjust the pH to 3.0. After incubation at room temperature for 10 min, the supernatant containing eluted phages was collected and neutralized to pH 8.5 by Tris buffer (pH 9.1).

Individual phage clones from the fourth and fifth rounds of biopanning were randomly selected, cultured and sequenced as published before (Chen, Z., et al., *Mol. Pharm.*, 2015, 12(6):2180-2188). Encoded peptides sequences were deduced from the phage DNA sequences.

Example 5

Cell phage ELISA. LNCaP and PC-3 cells were seeded in 96-well plates at a concentration of 2×10$^4$ cells per well. After 24 h, the cells were fixed with cold methanol-acetone (1:1, v/v). Phages suspended in RPMI 1640 medium were incubated with the fixed cells for 1 h, followed by washing with PBS to remove unbound phages. The cells were incubated with HRP conjugated anti-M13 monoclonal antibodies for 1 h. After adding TMB substrate, the absorbance at 450 nm was measured with a Beckman DTX 880 multimode Detector (Beckman coulter, Inc., Brea, Calif.).

Example 6

Binding affinity to various types of cells. LNCaP, PC-3, HSC-T6, and HeLa cells were detached using nonenzymatic cell dissociation solution and suspended in medium with 1% BSA at a density of 1×10$^7$ cells/mL. The suspended cells were incubated with the GTI phages at 4° C. for 1 h under gentle rotation. The cell suspension was then mixed with an organic phase composed of dibutyl phthalate and cyclohexane (9:1, v/v). After centrifugation at 10,000 RPM for 10 min, the mixture was snap frozen using liquid nitrogen. The bottom of the tube was sliced off, and bound phages in the cell pellet were recovered by infecting ER2738 bacteria.

Example 7

Competitive inhibition assay. Competitive binding inhibition between selected phages and their encoded peptides was examined in this study. LNCaP cells (1×10$^7$ cells/mL) suspended in RPMI-1640 medium were incubated with encoded peptides at 4° C. for 30 min under gentle rotation. The cells were then washed, resuspended in fresh RPMI-1640 medium containing phage clones, and incubated at 4° C. for 1 h. The bound phages were recovered and titered as described above.

Example 8

Flow cytometry analysis. Cells were detached using non-enzymatic cell dissociation solution and suspended in PBS (pH=7.4) at a concentration of 1×10$^6$ cells/mL. A series of concentrations (0.1-100 μM) of FAM-labeled peptides were incubated with 500 suspended cells at 4° C. for 1 h under gentle rotation. The cells were then washed with PBS for three times and subjected to fluorescence analysis on a FACSCalibur flow cytometer (BD Biosciences, Franklin Lakes, N.J.).

Example 9

Cellular uptake of FAM-labeled peptides Cells were seeded in 4-well chambers at a density of 5×10$^4$ cells per well and incubated at 37° C. for 24 h. The cells were then washed with PBS and then incubated with 10 μM FAM-labeled peptides in Opti-MEM medium at 37° C. for 1 h. After incubation, the cells were gently washed three times with DPBS, fixed with 10% formalin, and mounted with VECTASHIELD® mounting medium containing DAPI. Cellular uptake of the peptides was examined using a laser scanning confocal microscope (Leica TCS SP5).

Example 10

DHT (5-a-dihydrotestosterone) treatment. LNCaP cells were cultured in PRMI-1640 medium with 5% charcoal-stripped FBS (DHT free) for 24 h. Subsequently, the cells were incubated in 5% charcoal-stripped FBS PRMI-1640 medium containing 2 nM DHT for 48 h. FAM-labeled GTI peptide (10 μM) was incubated with DHT-treated LNCaP cells and normal LNCaP cells at 37° C. for 1 h. The cells were washed, fixed with 10% formalin, and mounted with VECTASHIELD® mounting medium containing DAPI. Cellular uptake of the GTI peptide was examined using a laser scanning confocal microscope (Leica TCS SP5).

The expressions of PSMA in the DHT-treated LNCaP and normal LNCaP cells were examined using western blot. Briefly, the cells were lysed on ice with RIPA buffer containing protease and phosphatase inhibitor cocktail. Protein concentrations were determined by a BCA protein assay kit. Equivalent amounts of protein (20 μg) were separated by a 12% SDS-PAGE gel. The proteins was transferred to PVDF membrane, blocked with 5% nonfat milk at room temperature for 2 h, and probed with the primary anti-PSMA antibody (Abcam, Cambridge, Mass.). The protein was then visualized with horseradish peroxidase-conjugated secondary antibody and the FluorChem FC2 imaging system (Alpha Innotech, CA).

Example 11

Biodistribution study. The animal protocol was approved by the University of Missouri-Kansas City, Institutional Animal Care and Use Committee (IACUC). The C4-2 xenograft tumor model was developed by subcutaneous injection of 1×10$^6$ C4-2 cells with matrigel into each flank of BALB/c nude male mice aged 5-6 weeks. Once the tumor is formed (~1 cm$^3$), 20 nmol FAM-labeled GTI peptide and its scrambled peptide (random permutation of the GTI peptide) were injected into the mice via tail vein. After two hours, the mice were sacrificed, and major organs including the tumors, liver, heart, spleen, lungs, kidneys, and muscle were harvested. Fluorescence intensity of these organs was examined using a Xenogen IVIS imaging system (Xenogen, Hopkinton, Mass.).

Example 12

Statistics analysis. Data were presented as the mean standard deviation (SD) or standard error (SE). Difference between any two groups was evaluated by ANOVA. P<0.05 is considered statistically significant.

Example 13

Figure 2:
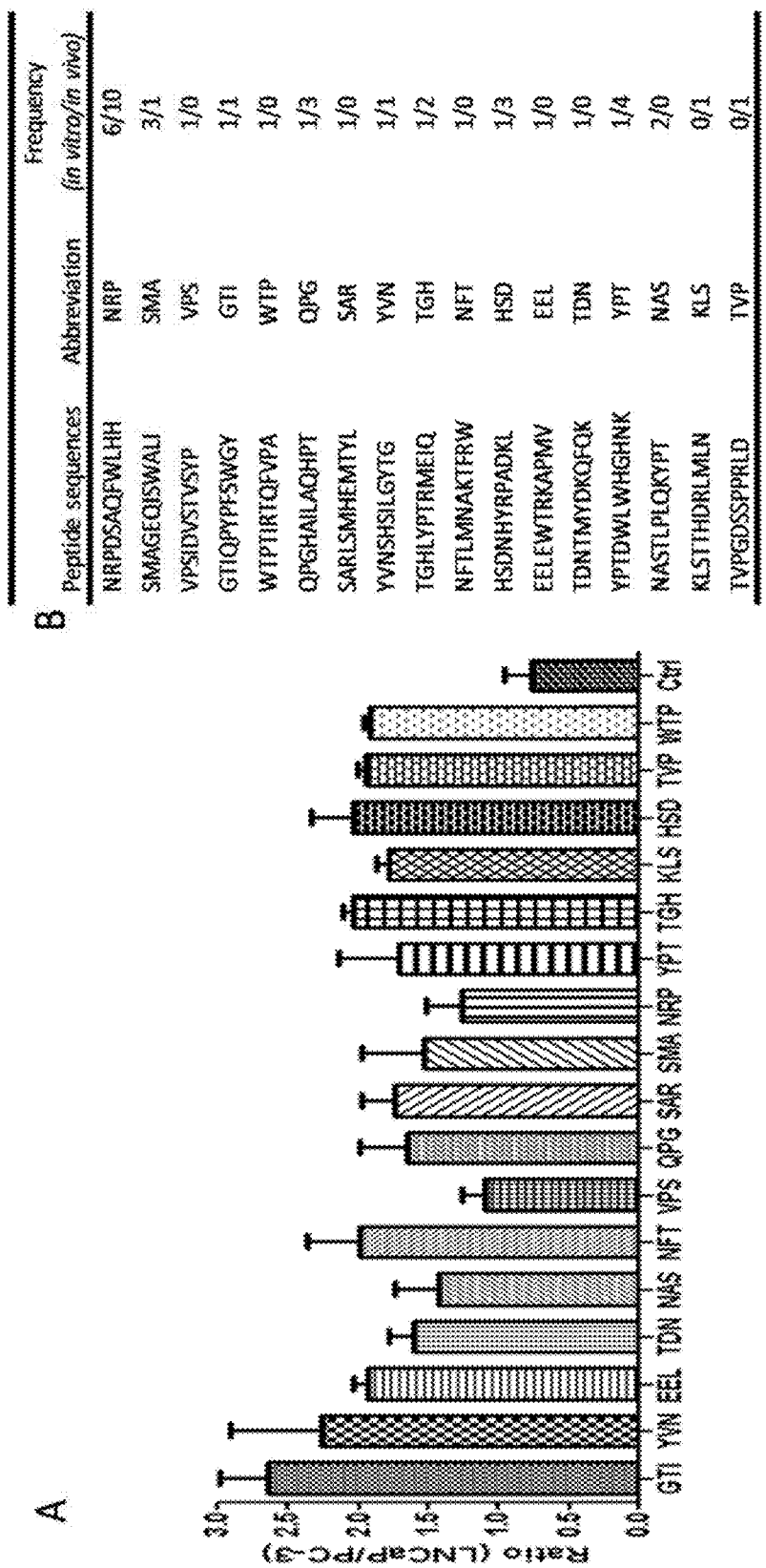
FIG. 2 displays the binding affinity of selected phage clones in LNCaP cells. (A) Binding of the phages on PSMA-positive LNCaP and PSMA-negative PC-3 cells that were examined using cell phage ELISA. The ratio of absorbance in LNCaP and PC-3 cells was calculated. Results are represented as the mean±SD (n=3). (B) Peptide sequences of the selected phage clones (SEQ ID NOS 4, 3, 15, 2, 16, 5, 17, 6, 7, 18, 8, 19, 20, 9 and 21-23, respectively, in order of appearance).

Identification of PSMA-specific peptides. A novel combinatorial phage biopanning procedure was developed to discover PSMA-specific peptides that can be potentially used as ligands for targeted drug delivery to prostate cancer. As shown in FIG. 1, five rounds of biopanning against recombinant human PSMA extracellular domain (ECD), PSMA-positive LNCaP cells, and LNCaP xenografts in nude mice were conducted. One hundred and twenty-two individual phage clones from the fourth and fifth rounds of biopanning were randomly selected and amplified. Binding affinities of these selected phage clones were examined in PSMA-positive LNCaP and PSMAnegative PC-3 cells using cell phage ELISA. The ratio of absorbance in LNCaP and PC-3 cells (LNCaP/PC-3) was calculated to identify phage clones that show higher binding affinity for LNCaP than PC-3 cells. Fifty phage clones with higher affinity for PSMA-positive LNCaP cells were selected and sequenced. These phage clones express 17 different peptide sequences which are listed in FIG. 2.

As shown in FIG. 2A, GTI phage encoding the peptide GTIQPYPFSWGY (SEQ ID NO: 2) shows the highest binding affinity to LNCaP cells. FIG. 2B lists the frequency of each peptide sequence in these fifty phages. The NRP phage encoding the peptide NRPDSAQFWLHH (SEQ ID NO: 4) repeats 6 times from in vitro biopanning and 10 times from in vivo biopanning. The phages encoding the peptides SMAGEQISWALI (SEQ ID NO: 3), GTIQPYPFSWGY (SEQ ID NO: 2), QPGHAILAQHPT (SEQ ID NO: 5), YVNSHSILGYTG (SEQ ID NO: 6), TGHLYPTRMEIQ (SEQ ID NO: 7), HSDNHYRPADKL (SEQ ID NO: 8), and YPTDWLWHGHNK (SEQ ID NO: 9) were also found not only in in vitro but also in vivo biopannings. Therefore, these eight phages were selected for further evaluation.

Figure 3:
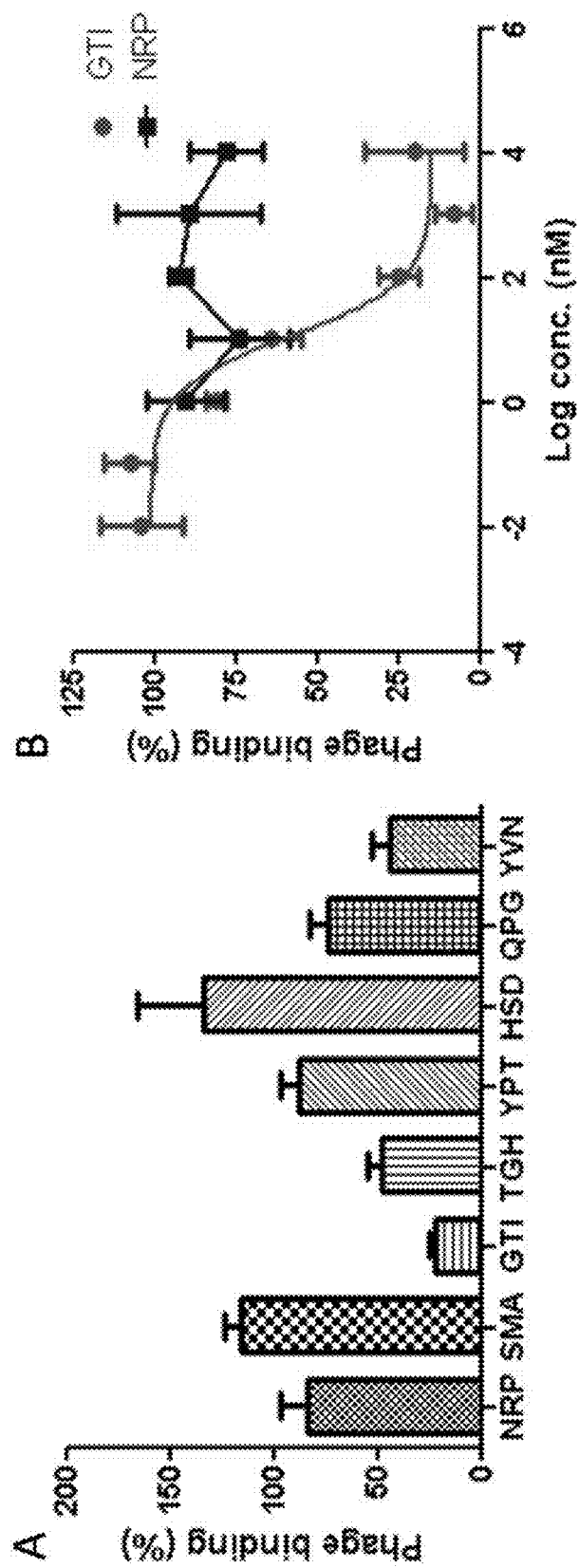
FIG. 3 shows the results of competitive inhibition of peptides and their corresponding phages. LNCaP cells were pre-incubated with synthetic peptides and then incubated with their corresponding phages. The bound phages were recovered and titered. (A) Competitive inhibition of eight selected peptides at 100 μM. (B) Competitive inhibition of the GTI and NRP peptide at a series of concentrations. Results are represented as the mean±SD (n=3).

Competitive inhibition of selected phages and their corresponding peptides. It was first evaluated whether these phages bind to LNCaP cells via specific interaction with their encoding peptides. LNCaP cells were pre-incubated with the encoding peptides, followed by washing and incubation with the corresponding phages. The bound phages were then eluted and titered. As shown in FIG. 3A, the GTI peptide shows the highest competitive inhibition to its corresponding phage. The TGH and YVN peptides exhibit relatively weaker competitive inhibition compared to the GTI peptide, while competitive inhibition of the peptides SMA, HSD, QPG, YPT and NRP are negligible. FIG. 3B further illustrates the competitive inhibition effect of the GTI and NRP peptides at various concentrations. The GTI peptide exhibits a concentration dependent inhibition to its corresponding phage, while the NRP peptide does not affect the binding of its corresponding phage to LNCaP cells. This result may suggest that the GTI phage binds to LNCaP via the same receptor as its peptide, while the NRP phage may bind to LNCaP via a different moiety as its encoding peptide.

Example 14

Figure 4:
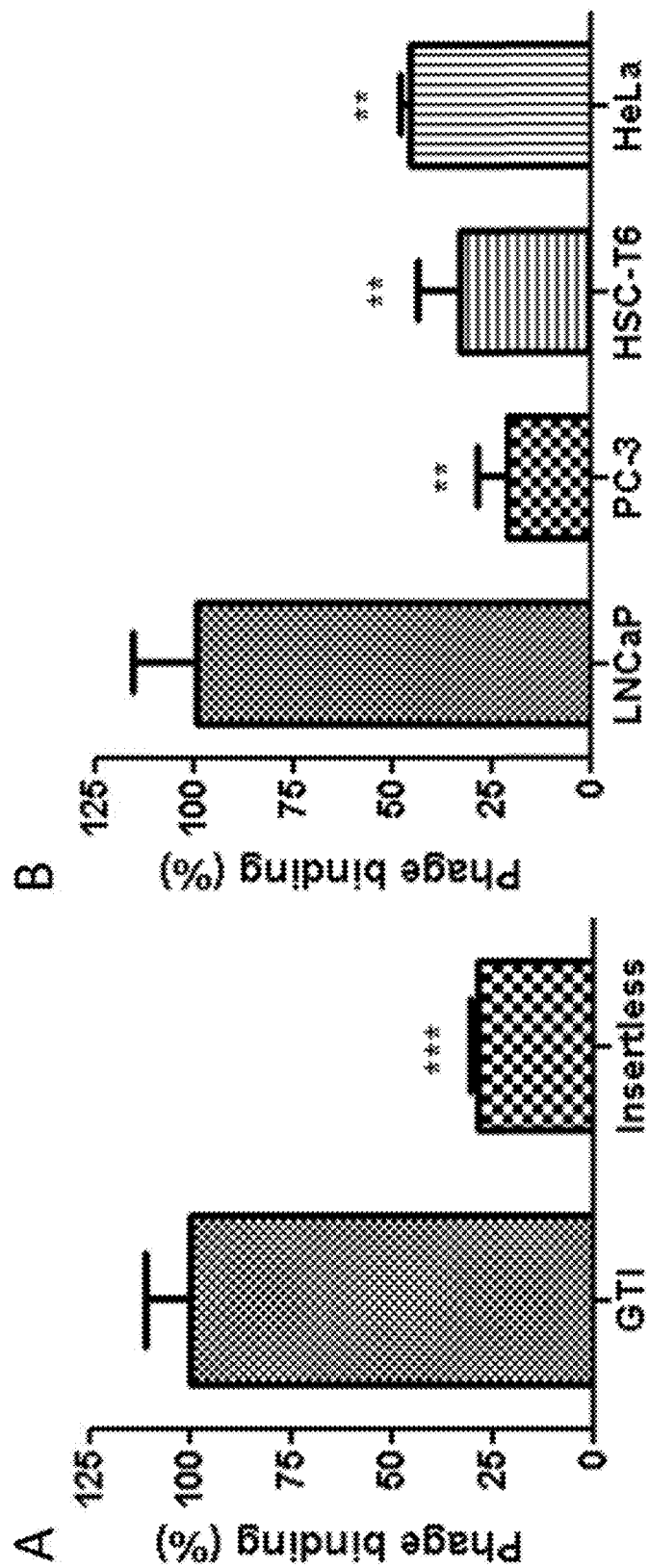
FIG. 4 shows the binding affinity of the GTI phage in LNCaP and PSMA-negative cells. The cells were suspended and incubated with the GTI phage at 4° C. for 1 h, and the bound phages were eluted and titered. The number of GTI phages that bound to LNCaP cells was normalized as 100%. (A) Binding of the GTI phage and an insertless phage in LNCaP cells. (B) Binding of the GTI phage in PSMA-positive LNCaP cells and PSMA-negative cells. Results are represented as the mean±SD (n=3). (*$p<0.001$, $p<0.01$).

Binding affinity and specificity of the GTI phage to PSMA-Positive LNCaP cells. Next. the binding affinity of the GTI phage was compared to PSMA-positive LNCaP and PSMA-negative cells. Compared to insertless phage, which does not encode a peptide, the GTI phage exhibits a much higher binding affinity to LNCaP cells (FIG. 4A). In addition, the GTI phage exhibits higher affinity to LNCaP cells than to PSMA-negative cells (FIG. 4B), which may further indicate that the GTI phage specifically binds to PSMA on LNCaP cells.

Example 15

Figure 5A:
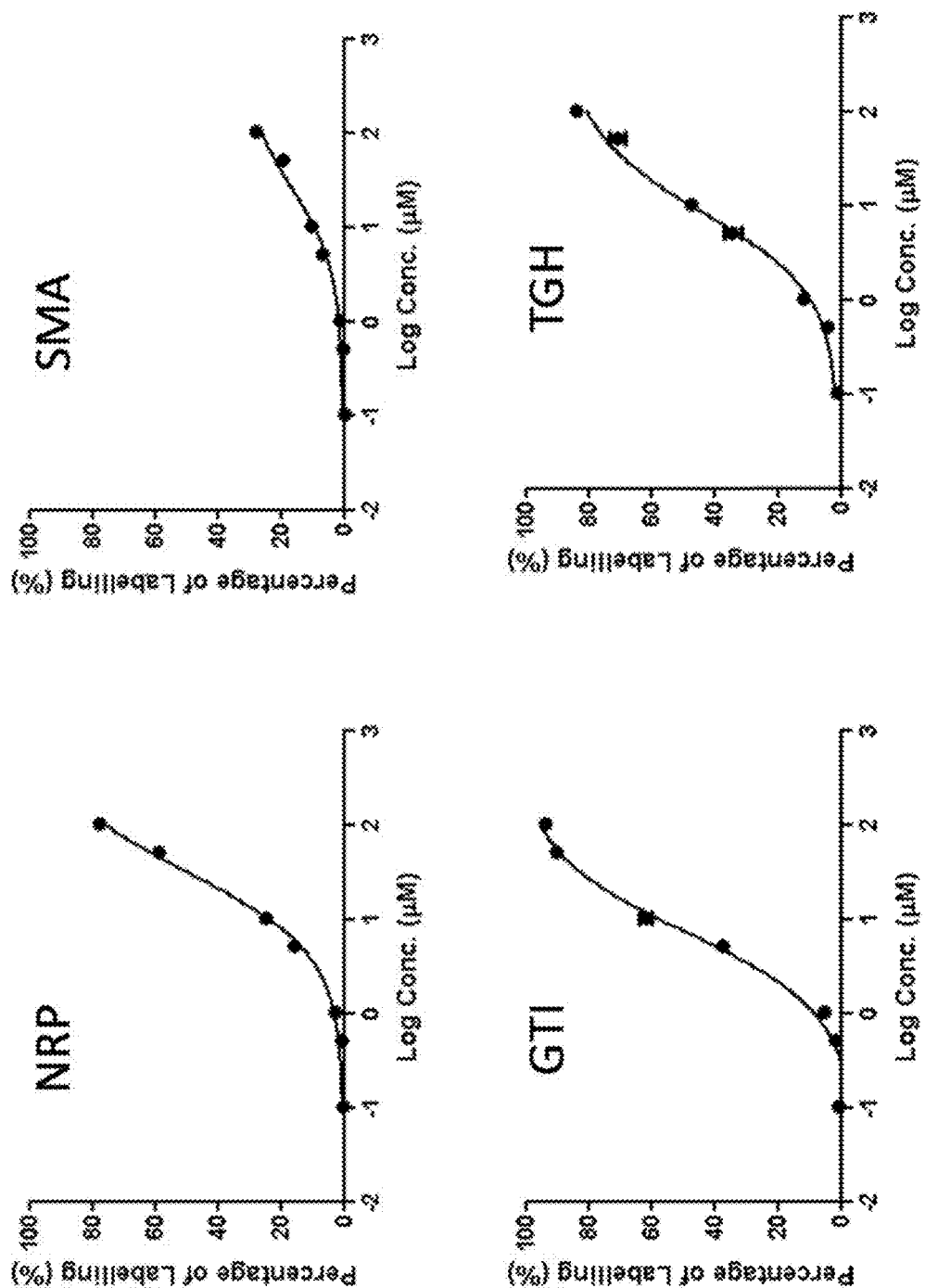
FIG. 5A shows the binding affinity of the peptides NRP, SMA, GTI, and TGH in LNCaP cells. The cells were suspended and incubated with a series of concentrations of FAM-labeled peptides at 4° C. for 1 h. The cells were then subjected to flow cytometry analysis to determine the percent of cells that take up the peptides. Equilibrium dissociation curves of the selected peptides in LNCaP cells are displayed. Results are represented as the mean±SD (n=3).
Figure 5B:
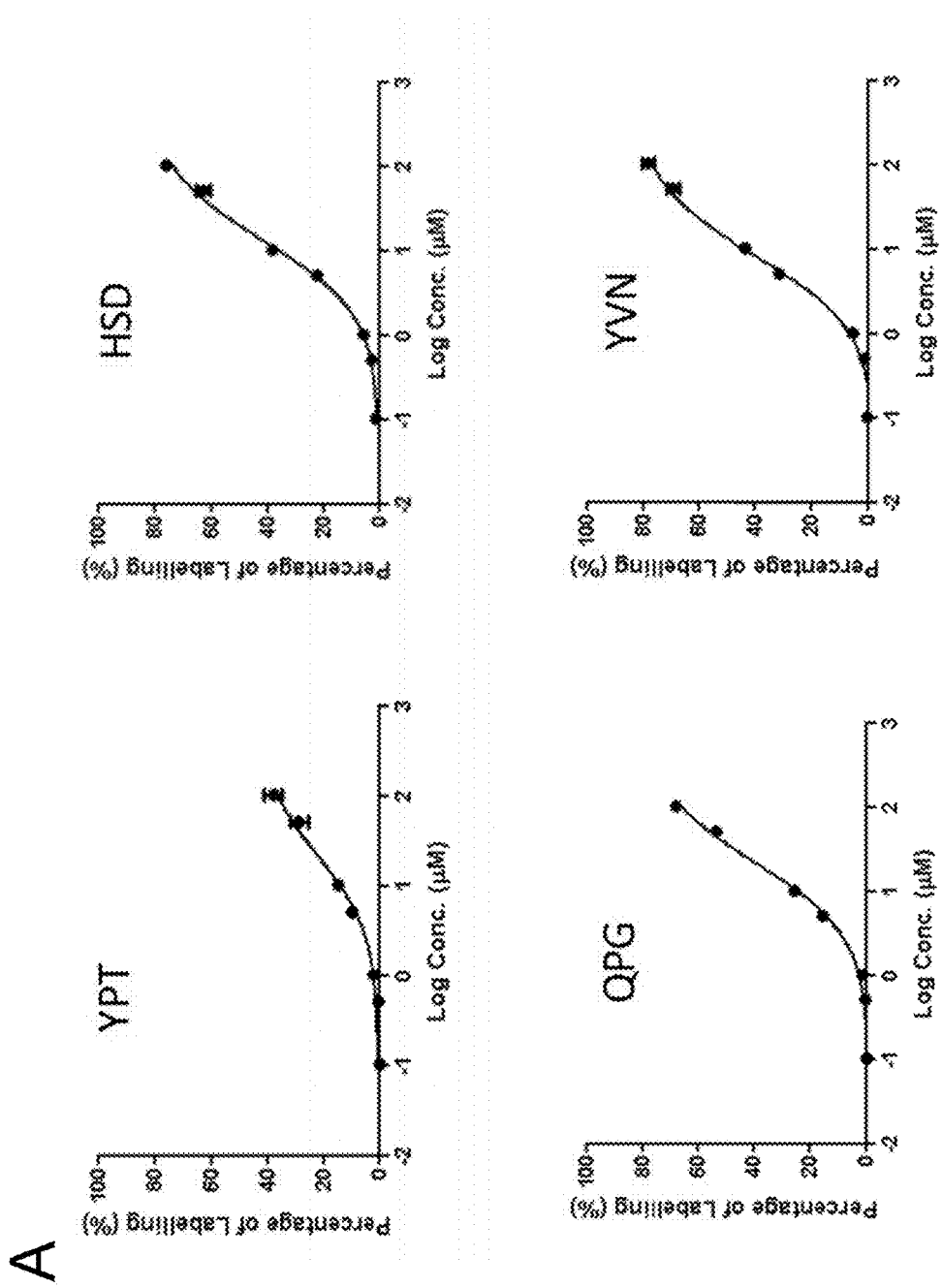
FIG. 5B shows the binding affinity of the peptides YPT, HSD, QPG, and YVN in LNCaP cells. The cells were treated and analyzed as described above for FIG. 5A. Equilibrium dissociation curves of the selected peptides in LNCaP are displayed.
Figure 5C:
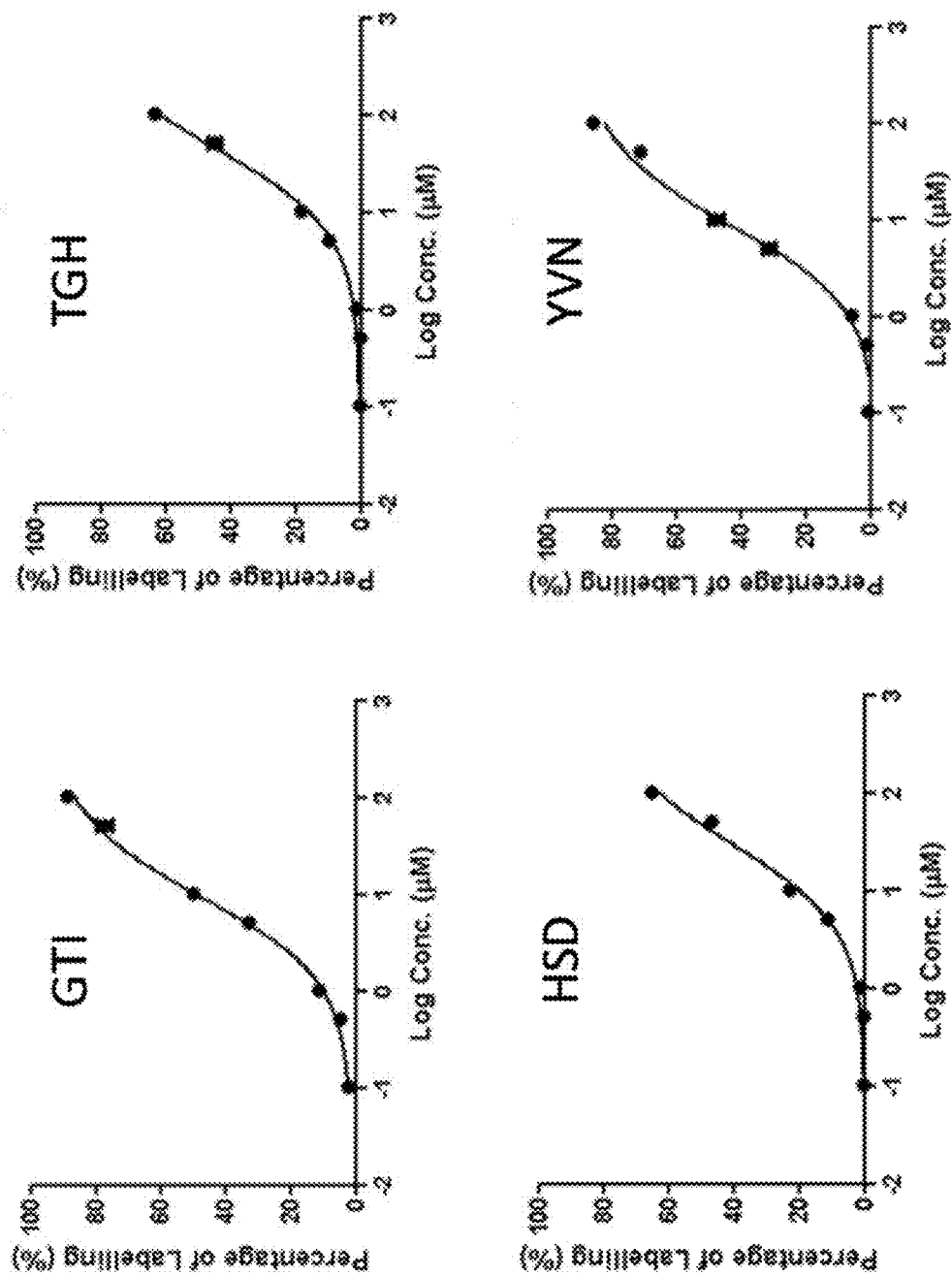
FIG. 5C shows the binding affinity of the peptides GTI, TGH, HSD, and YVN in C4-2 cells. The cells were treated and analyzed as described above for FIG. 5A. Equilibrium dissociation curves of the selected peptides in C4-2 cells are displayed.
Figure 5E:
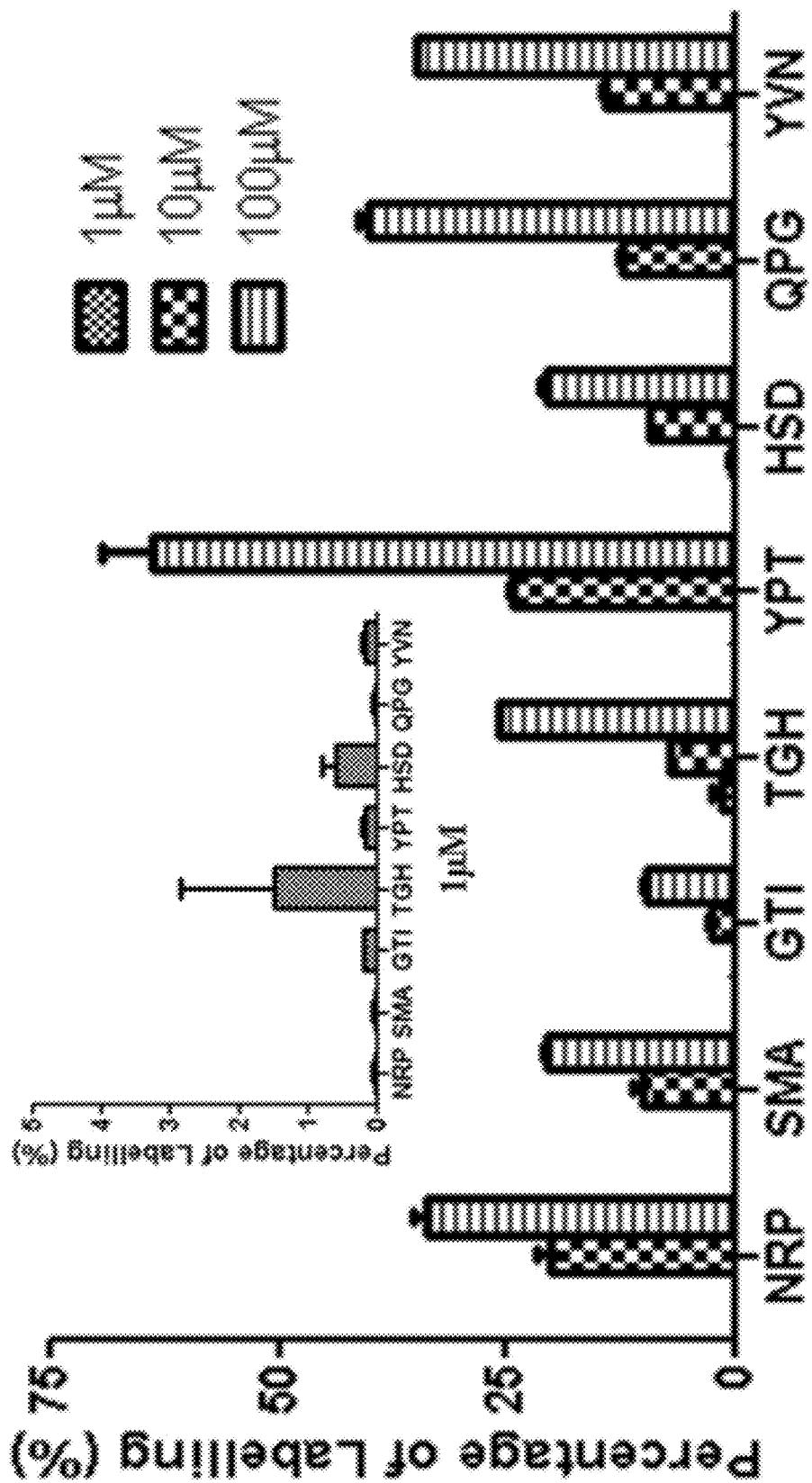
FIG. 5E displays binding results of the peptides (1 µM, 10 µM and 100 µM) in PC-3 cells.

Apparent equilibrium dissociation constant ($K_d$) of the peptides. To quantitate the apparent affinity of phage encoding peptides to prostate cancer cells, FAM-labeled peptides were incubated with PSMA-positive LNCaP cells at different concentrations. Flow cytometry was employed to determine the percentage of cells that were labeled with the peptides. The apparent $K_d$ values were calculated by fitting to a one-site specific binding model using GraphPad Prism 5. As illustrated in FIG. 5A, FIG. 5B, and FIG. 5D, the HSD, GTI, TGH, and YVN peptides exhibit higher binding affinity compared to other peptides. This is in accordance with the results of their corresponding phages in FIGS. 2 and 3. Their apparent $K_d$ values against LNCaP cells are 12.80 μM, 8.22 μM, 8.01 μM, and 9.34 μM, respectively. Also, the apparent $K_d$ values of HSD, GTI, TGH, and YVN were examined in another PSMA-positive prostate cancer C4-2 cell line (FIG. 5C and FIG. 5D). The GTI and YVN peptides show similar affinity to C4-2 as to LNCaP cells, while the HSD and TGH peptides exhibit less affinity to C4-2 cells compared to LNCaP cells. Binding affinities of these FAM-labeled peptides in PC-3 cells are presented in FIG. 5E. The GTI peptide shows the lowest biding affinity in PC-3, which may indicate its high specificity to PSMA-positive cells. As a result, the GTI peptide was selected as the best PSMA-specific ligand for following studies.

Example 16

Figure 6:
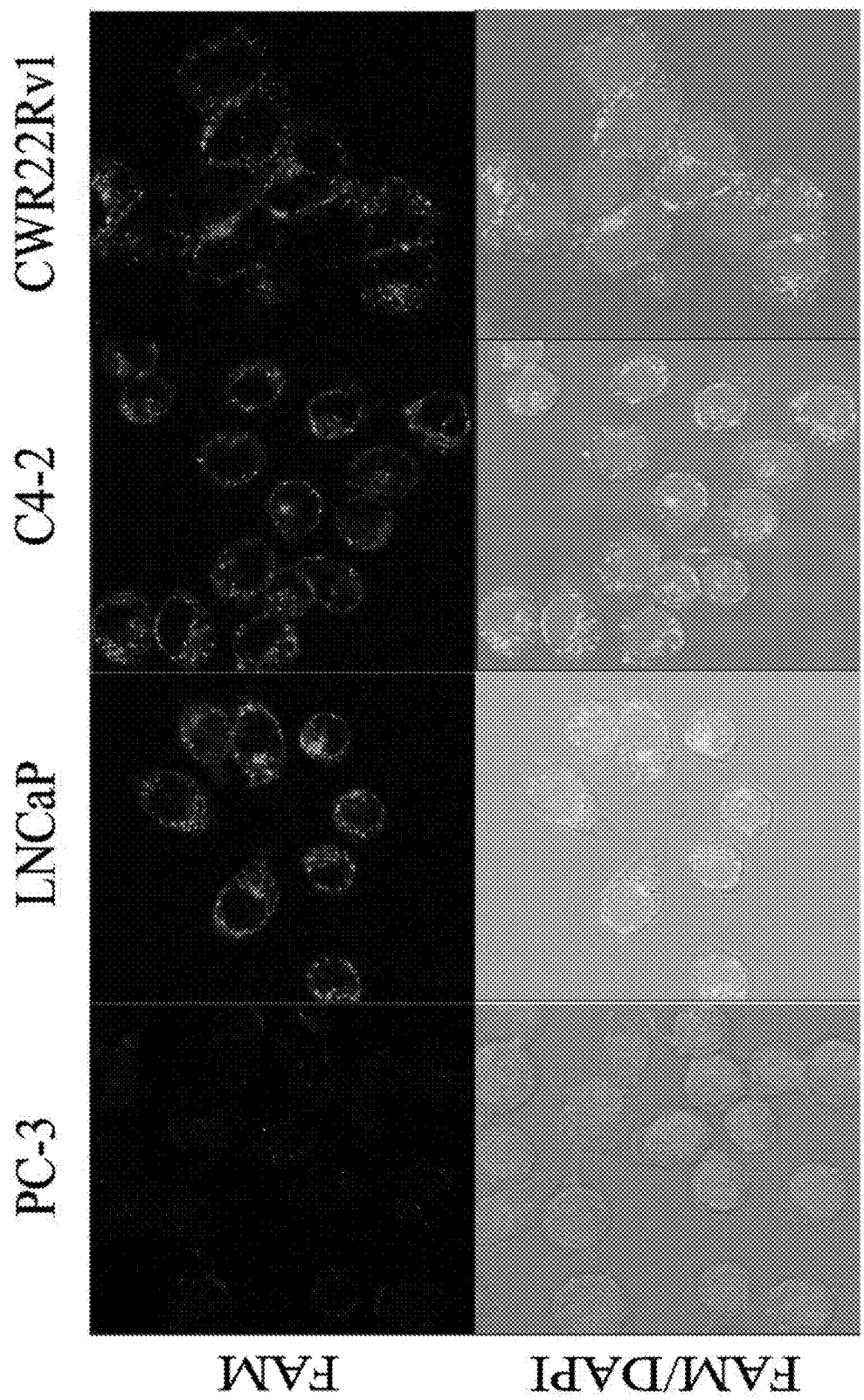
FIG. 6 displays the results of the cellular uptake of the FAM-labeled GTI peptide in PSMA positive and negative cells. The FAM-labeled GTI peptide was incubated with the cells at 37° C. for 1 h, followed by washing with PBS and examination under a confocal microscope.

Cellular uptake of FAM-labeled GTI peptide in various PSMA-Positive Cells. Next, cellular uptake of the FAM-labeled GTI peptide was evaluated in three PSMA-positive cells, including LNCaP, C4-2 and CWR22Rv1. PSMA-negative PC-3 cells were used as a control. As illustrated in FIG. 6, the GTI peptide shows high uptake in all three PSMA-positive cells, while its uptake in PC-3 cells is negligible.

Figure 7:
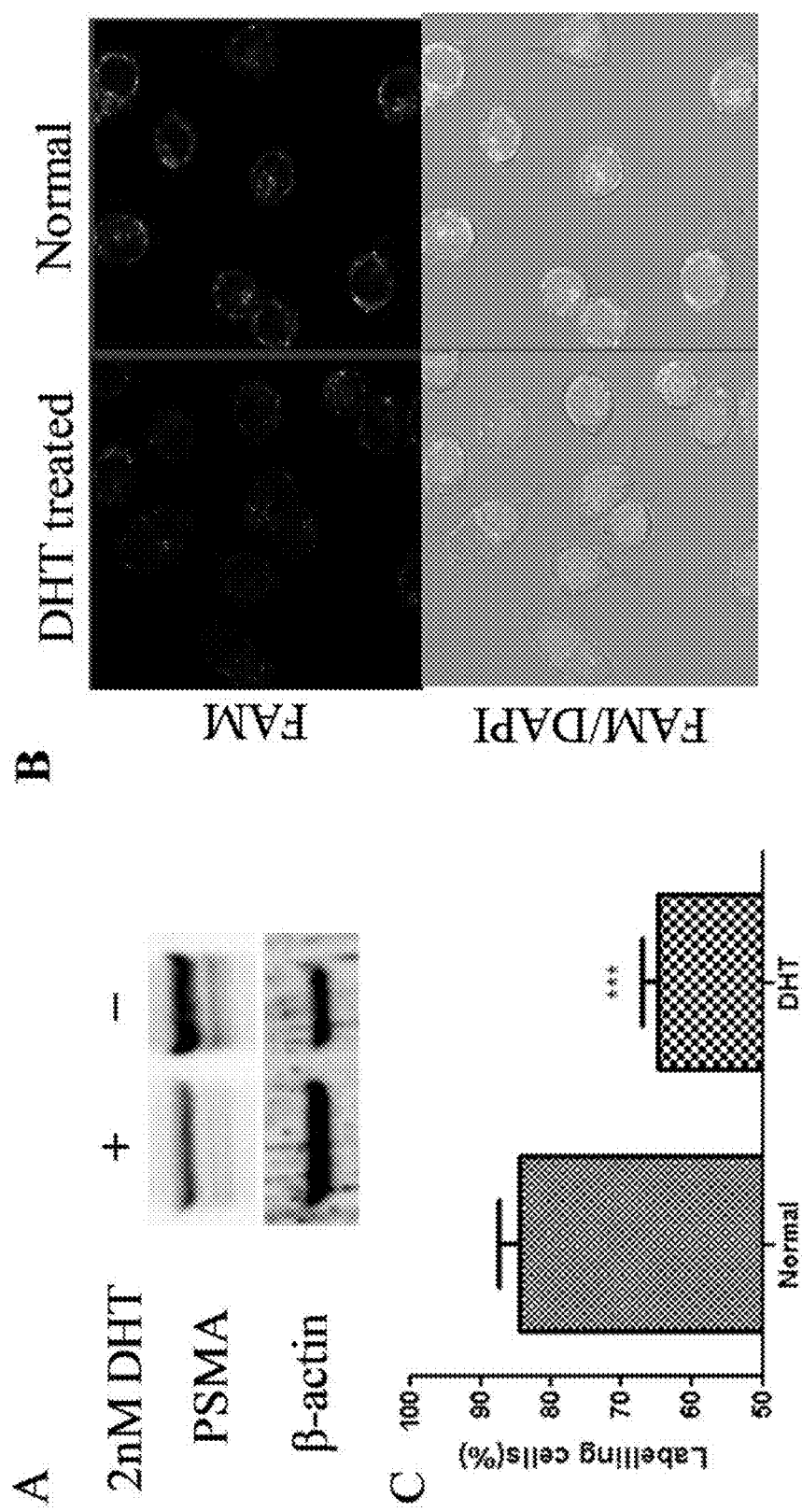
FIG. 7 displays the results of downregulating the expression of PSMA, which inhibits cellular uptake of the FAM-labeled GTI peptides in LNCaP cells. LNCaP cells were treated with 2 nM DHT before the cellular uptake study to downregulate the expression of PSMA. LNCaP cells without DHT treatment were used as the control. (A) The expression of PSMA in normal and DHT treated LNCaP cells was examined using western blot. (B) LNCaP cells were incubated with 10 µM FAM-labeled GTI peptide at 37° C. for 1 h and then examined under a confocal microscope. (C) Suspended LNCaP cells were incubated with FAM-labeled GTI peptide at 4° C. for 1 h, followed by flow cytometry analysis to determine cellular uptake. Results are represented as the mean±SD (n=3). (***p<0.001).

To determine whether cellular uptake of the GTI peptide is mediated by PSMA, the expression of PSMA in LNCaP cells was downregulated using 5-a-dihydrotestosterone (DHT) (FIG. 7A) (McNamara $2^{nd}$, J. O., et al., Nat. Biotechnol., 2006, 24(8):1005-1015; Israeli, R. S., et al., Cancer Res., 1994, 54(7):1807-1811) and then examined the uptake of the FAM-labeled GTI peptide. As shown in the confocal images (FIG. 7B), uptake of the GTI peptide in DHT-treated LNCaP cells is much lower compared to that in untreated LNCaP cells. Flow cytometry assay (FIG. 7C) shows a similar result. The percentage of cells labeled by the GTI peptide is significantly reduced when the expression of PSMA is downregulated by DHT. These results clearly demonstrate that the GTI peptide is a PSMA-specific ligand.

Example 17

Figure 8:
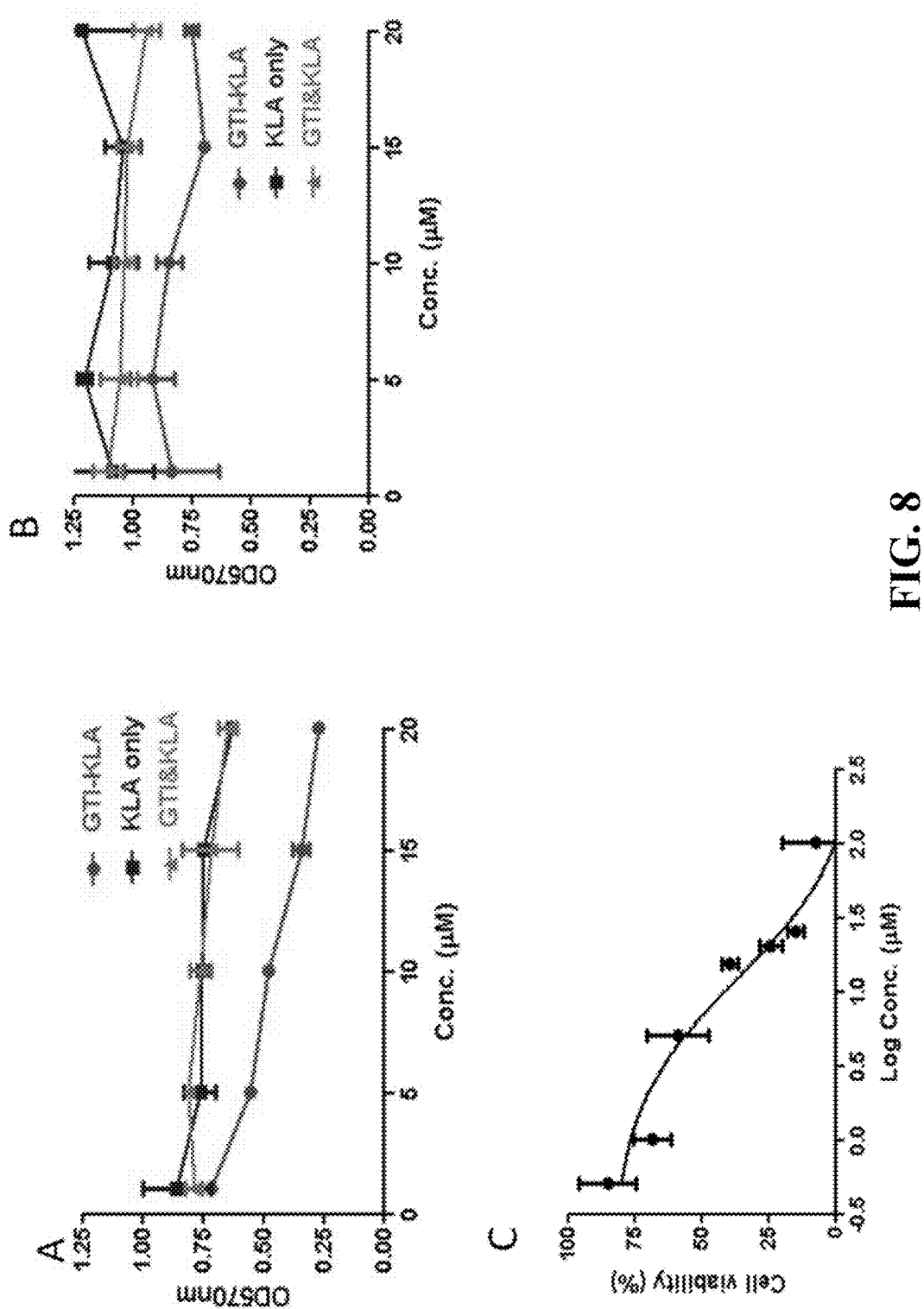
FIG. 8 shows that the GTI peptide enhances the uptake and apoptotic effect of a proapoptotic peptide (KLA) in PSMA-positive cells. The GTI/KLA fusion peptide, the mixture of GTI and KLA peptides, and KLA peptide were incubated with the PSMA-positive LNCaP cells (A) and PAMS-negative PC-3 cells (B) for 48 h, followed by MTT assay to determine the apoptotic effect. The viability concentration-response curve of the GTI/KLA fusion peptide in LNCaP cells was presented in (C). Results are represented as the mean±SD (n=3).

The GTI Peptide Enhances the Uptake and Apoptotic Effect of a Proapoptotic Peptide. The objective of this study was to identify a PSMA-specific peptide that can be used a targeting ligand to deliver various therapeutic agents into PSMA-positive prostate cancer cells. It was therefore critical to demonstrate that the GTI peptide can deliver a cargo to prostate cancer cells. The antimicrobial proapoptotic peptide KLAKLAKKLAKLAK (KLA) (SEQ ID NO: 10) was therefore used as a model drug in this study. Once inside cells, the KLA peptide can induce mitochondrial disruption and cellular toxicity by triggering permeabilization and swelling of the mitochondria. However, the KLA peptide itself cannot enter the cell. Instead, it has to be fused with a protein transduction domain to exert its apoptotic activity (see: Javadpour, M. M., et al., *J. Med. Chem.*, 1996, 39(16): 3107-3113; Mai, J. C., et al., *Cancer Res.*, 2001, 61(21): 7709-7712). For the purpose of the invention herein, a GTI-KLA fusion peptide was designed and its proapoptotic activity in LNCaP and PC-3 cells was evaluated. A series of concentrations of the fusion peptide GTI-KLA, the mixture of GTI and KLA peptides, and the KLA peptide were incubated with LNCaP cells and PC-3 cells for 48 h. As FIG. 8A indicates, the GTI-KLA fusion peptide demonstrates cytotoxicity in LNCaP cells, whereas no cytotoxicity was observed in either the mixture of GTI KLA peptides or the KLA peptide alone up to 20 µM. Meanwhile, the GTI-KLA fusion peptide does not show cytotoxicity in PC-3 cells (FIG. 8B), which may indicate that the fusion peptide enters LNCaP cells via PSMA. The $IC_{50}$ of the GTI-KLA fusion peptide in LNCaP cells is approximately 12.10 µM (FIG. 8C). This study demonstrates the potential of using the GTI peptide as a PSMA-specific ligand to deliver therapeutic agents to prostate cancer cells.

Example 18

Figure 9:
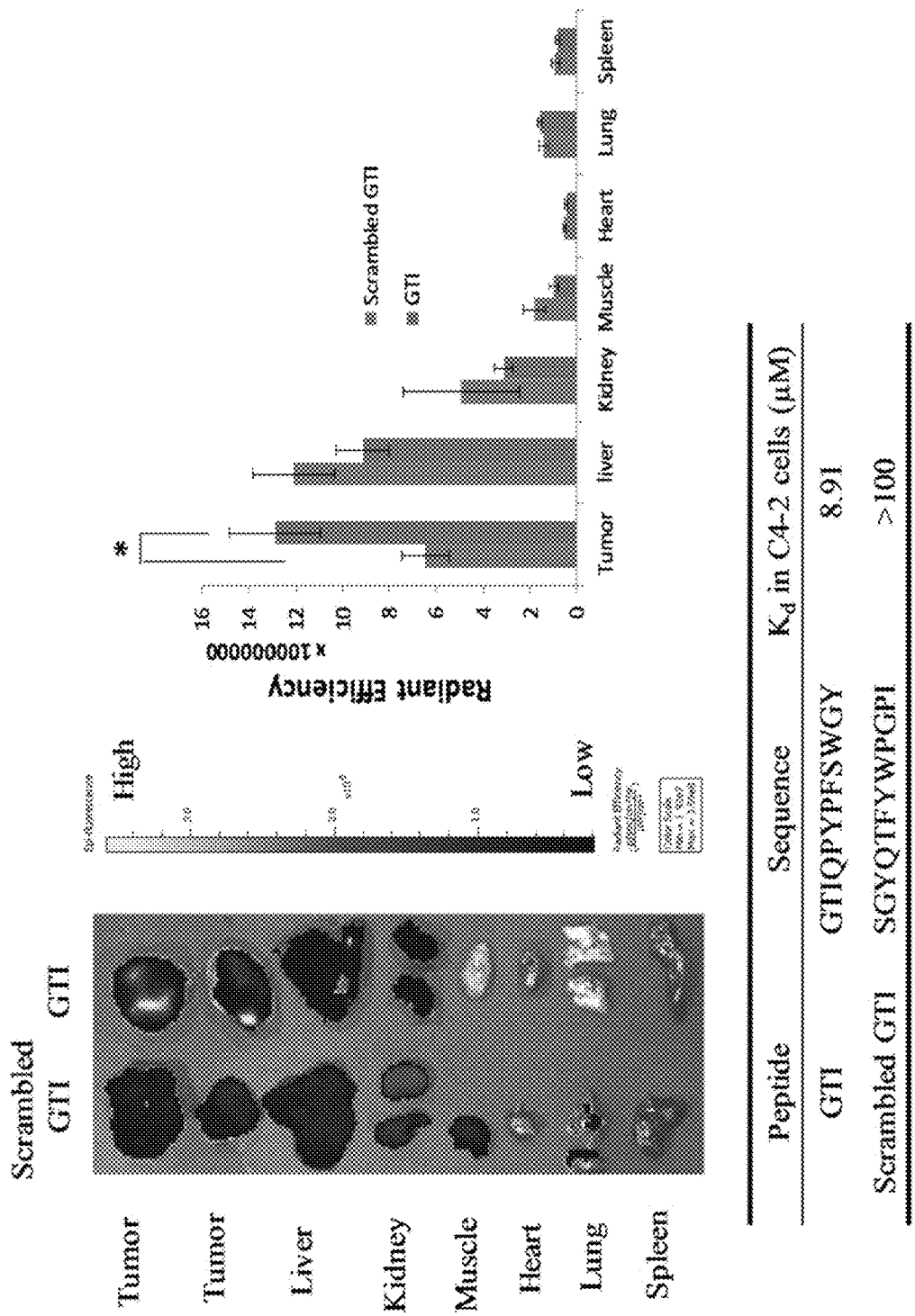
FIG. 9 shows the biodistribution of the GTI peptide (SEQ ID NO: 2) and its scrambled peptide (SEQ ID NO: 13) in nude mice bearing prostate cancer xenografts. The apparent $K_d$ values of the GTI peptide and its scrambled form in C4-2 cells were determined using flow cytometry. FAM-labeled GTI and its scrambled peptides were injected into nude mice bearing C4-2 xenograft tumors via the tail vein. The mice were sacrificed two hours post-administration, and major organs including the tumor, liver, kidneys, muscle, heart, lungs, and spleen were harvested for fluorescence imaging using a Xenogen IVIS imaging system. Data are presented as the mean±SE (n=4). (*p<0.05).

Biodistribution study. In order to evaluate the distribution profile of the GTI peptide in vivo, 20 nmol of FAM-labeled GTI peptide (GTIQPYPFSWGY (SEQ ID NO: 2)) and its scrambled peptide (random permutation of the GTI peptide, SGYQTFYWPGPI (SEQ ID NO: 13)) were injected into nude mice bearing subcutaneous C4-2 xenograft tumor via the tail vein. The GTI peptide exhibits lower apparent $K_d$ in C4-2 prostate cancer cells compared to its scrambled peptide (FIG. 9). It has been reported that peptide achieves its highest uptake in tissues 2 h post-administration (Chen, x., et al., *Cancer Res.*, 2004, 64(21):8009-8014), therefore the mice were sacrificed at 2 h post-administration and major organs harvested including the tumor, liver, kidneys, muscle, heart, lungs, and spleen. As illustrated in FIG. 9, the GTI peptide shows higher uptake in the tumors than other tissues including the liver and kidneys, which are the major sites for peptide metabolism (see: Carone, F. A., et al., *Am. J. Physiol.*, 1980, 238(3):F151-F158). Uptake of the GTI peptide in other organs, such as the heart, lungs and muscle is negligible. Moreover, the GTI peptide exhibits much higher uptake in the tumors in comparison to its scrambled peptide. On the contrary, the scrambled peptide shows the highest uptake in the liver. These results demonstrate that the GTI peptide can specifically bind to PSMA overexpressing C4-2 xenografts in vivo, suggesting its potential promise as a PSMA-specific ligand for prostate cancer targeted drug delivery.

Example 19

Figure 10A:
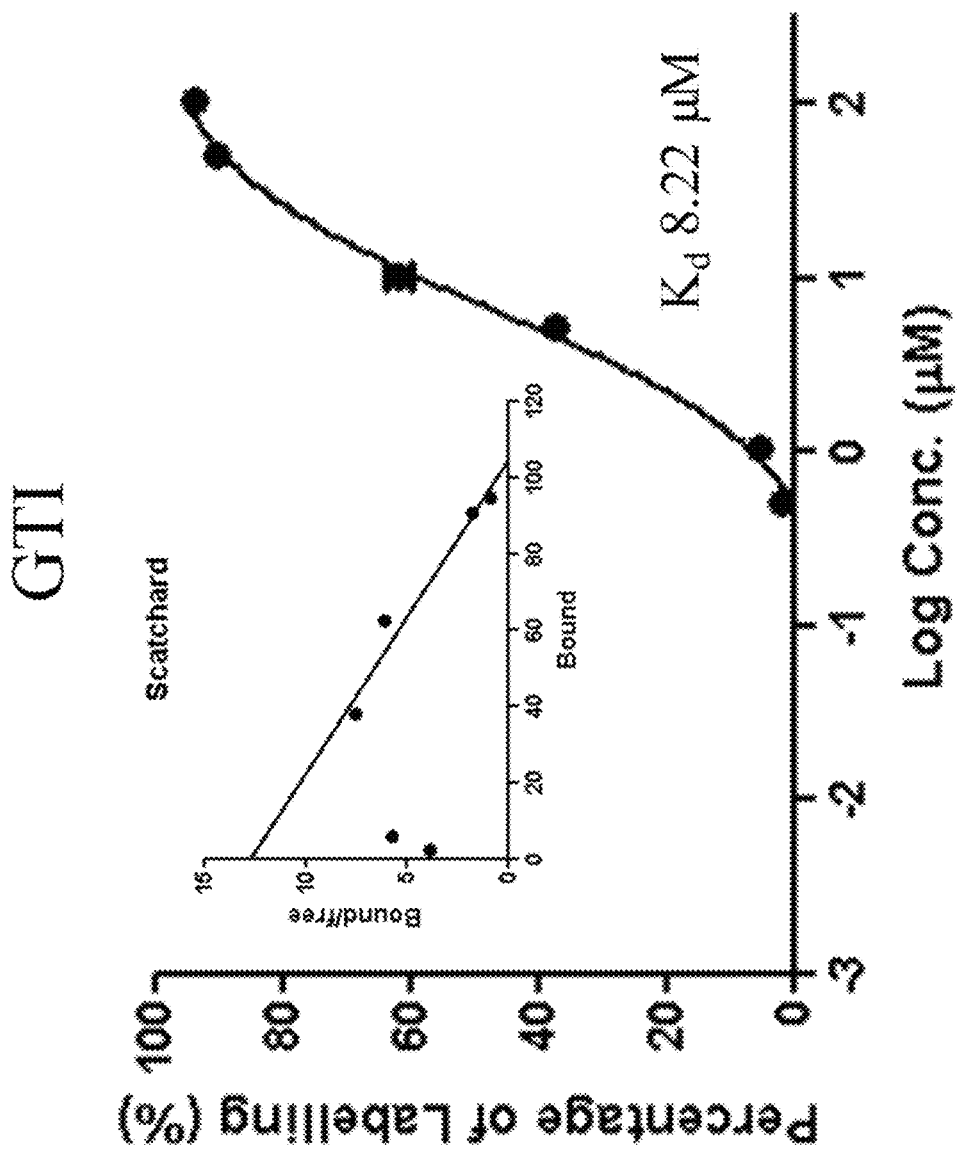
FIG. 10A shows the binding affinity of the prostate cancer specific peptide GTI in LNCaP cells. LNCaP cells were suspended and incubated with a series of concentrations of the peptides at 4° C. for 1 h, followed by flow cytometry analysis to determine cellular uptake. Results are represented as the mean±SD (n=3).
Figure 10B:
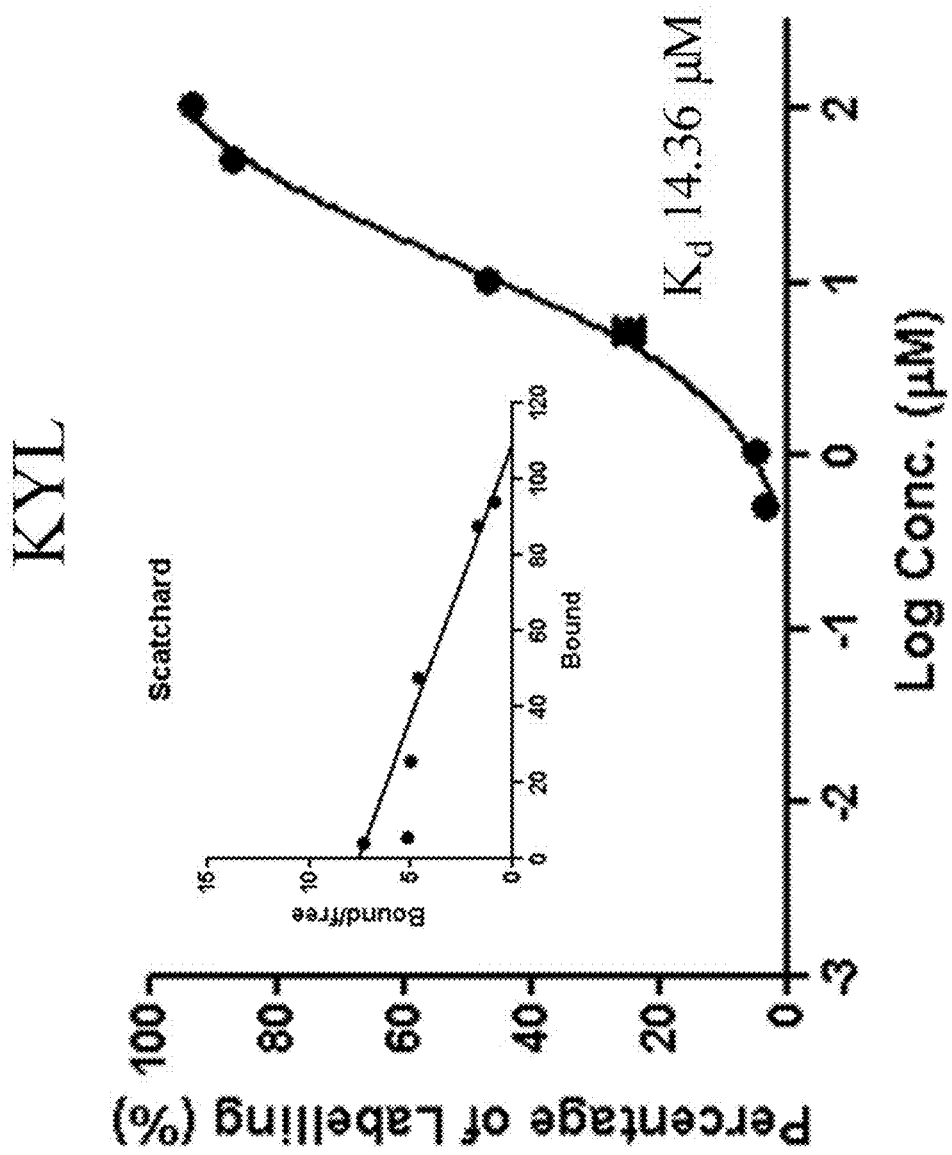
FIG. 10B shows the binding affinity of the prostate cancer specific peptide KYL in LNCaP cells. The cells were treated and analyzed as described above for FIG. 10A.
Figure 10C:
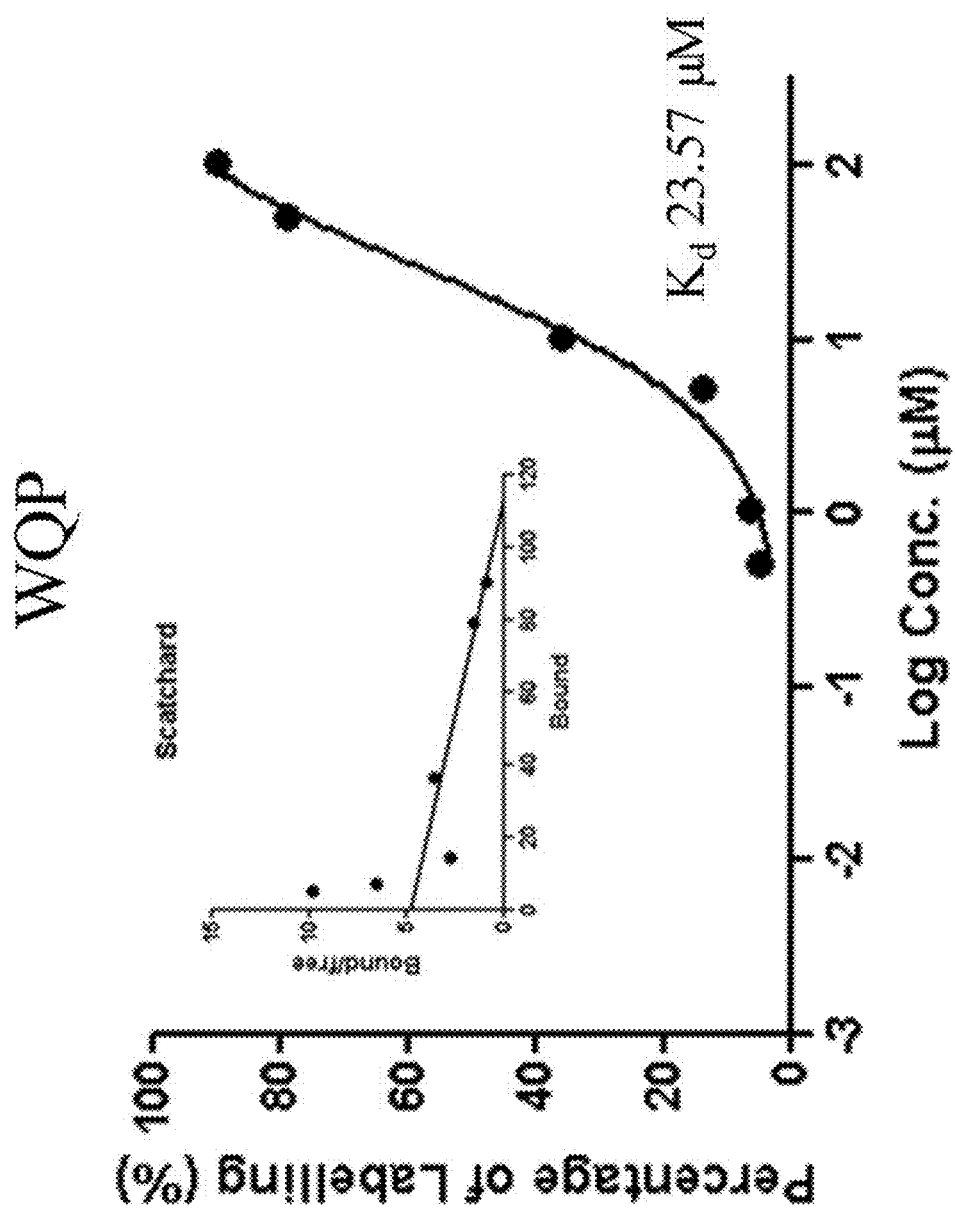
FIG. 10C shows the binding affinity of the prostate cancer specific peptide WQP in LNCaP cells. The cells were treated and analyzed as described above for FIG. 10A.

Comparison of the GTI peptides with other prostate cancer specific Peptides. Applicants have recently discovered a peptide KYLAYPDSVHIW (KYL) (SEQ ID NO: 14) that can specifically bind to LNCaP cells (see: Qin, B., et al., *Pharm. Res*, 2011, 28(10):2422-2434). WQPDTAHHWATL (WQP) (SEQ ID NO: 1) is another peptide that is reported to bind to the catalytic site of PSMA and inhibit its enzymatic activity (see: Aggarwal, S., et al., *Cancer Res.*, 2006, 66(18):9171-9177). Therefore, a comparison was performed of the apparent binding affinity of FAM-labeled GTI, KYL, and WQP peptides to LNCaP cells. As shown in FIG. 10A, FIG. 10B, and FIG. 10C, the GTI peptide exhibits the highest binding affinity to LNCaP cells with an apparent $K_d$ of 8.22 µM, while the apparent $K_d$ values of KYL and WQP peptides are 14.36 and 23.57 µM, respectively.

As can be easily understood from the foregoing, the basic concepts of the present invention may be embodied in a variety of ways. The invention involves numerous and varied embodiments of treatments of the conditions described herein, and the like.

As such, the particular embodiments or elements of the invention disclosed by the description or shown in the figures or tables accompanying this application are intended to be exemplary of the numerous and varied embodiments generically encompassed by the invention or equivalents encompassed with respect to any particular element thereof. In addition, the specific description of a single embodiment or element of the invention may not explicitly describe all embodiments or elements possible; many alternatives are implicitly disclosed by the description and figures.

It should be understood that each element of an apparatus or each step of a method may be described by an apparatus term or method term. Such terms can be substituted where desired to make explicit the implicitly broad coverage to which this invention is entitled. As but one example, it should be understood that all steps of a method may be disclosed as an action, a means for taking that action, or as an element which causes that action. Similarly, each element of an apparatus may be disclosed as the physical element or the action which that physical element facilitates. As but one example, the disclosure of a "treatment" should be understood to encompass disclosure of the act of a "treating", whether explicitly discussed or not; and, conversely, the disclosure of an act of "treating", whether explicitly discussed or not, should be understood to encompass disclosure of a "treatment" and even a "means for treating." Such alternative terms for each element or step are to be understood to be implicitly included in the description.

In addition, as to each term used, it should be understood that unless its utilization in this application is inconsistent with such interpretation, common dictionary definitions should be understood to be included in the description for each term as contained in the Random House Webster's Unabridged Dictionary, second edition, each definition hereby incorporated by reference.

All numeric values herein are assumed to be modified by the term "about", whether or not explicitly indicated. For the purposes of the present invention, ranges may be expressed as from "about" one particular value to "about" another particular value. When such a range is expressed, another embodiment includes from the one particular value to the other particular value. The recitation of numerical ranges by endpoints includes all the numeric values subsumed within that range. A numerical range of one to five includes, for example, the numeric values 1, 1.5, 2, 2.75, 3, 3.80, 4, 5, and so forth. It will be further understood that the endpoints of each of the ranges are significant both in relation to the other endpoint and independently of the other endpoint. When a value is expressed as an approximation by use of the antecedent "about," it will be understood that the particular value forms another embodiment. The term "about" generally refers to a range of numeric values that one of skill in the art would consider equivalent to the recited numeric value or having the same function or result. Similarly, the antecedent "substantially" means largely, but not wholly, the same form, manner or degree and the particular element will have a range of configurations as a person of ordinary skill in the art would consider as having the same function or result. When a particular element is expressed as an approximation by use of the antecedent "substantially," it will be understood that the particular element forms another embodiment.

It is to be understood that, as used herein, the grammatical conjunction "and/or" refers throughout to either or both of the stated possibilities.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Moreover, for the purposes of the present invention, the term "a" or "an" entity refers to one or more of that entity unless otherwise limited. As such, the terms "a" or "an", "one or more" and "at least one" can be used interchangeably herein.

Also, for the purposes of the present invention, it is to be understood that the volume units "mL" and "cc" are considered to be approximately equal. As such, these units can be used interchangeably herein.

The term "therapeutically effective amount" as used herein, refers to that amount of active compound or pharmaceutical agent that elicits the desired biological or medicinal response in a tissue system, animal, or human that is being sought by a researcher, veterinarian, medical doctor, or other clinician, which includes alleviation of the symptoms of the disease or condition being treated. In one aspect, the therapeutically effective amount is that which may treat or alleviate the disease/condition or symptoms of the disease/condition at a reasonable benefit/risk ratio applicable to any medical treatment. However, it is to be understood that the total daily usage of the compounds and compositions described herein may be decided by the attending physician within the scope of sound medical judgment. The specific therapeutically-effective dose level for any particular patient will depend upon a variety of factors, including the condition being treated and the severity of the condition; activity of the specific compound employed; the specific composition employed; the age, body weight, general health, gender, and diet of the patient; the time of administration, route of administration, and rate of excretion of the specific compound employed; the duration of the treatment; drugs used in combination or coincidentally with the specific compound employed; and like factors well known to the researcher, veterinarian, medical doctor, or other clinician of ordinary skill.

In addition, in those embodiments described herein drawn to combination therapy comprising administration of the therapeutic composition of the invention and one or more other drugs or agents, "therapeutically effective amount" refers to that amount of the combination of agents taken together so that the combined effect elicits the desired biological or medicinal response. For example, the therapeutically effective amount of the therapeutic composition of the invention and the one or more other drugs or agents, would be the total amount of the combination of agents that when taken together or sequentially, have a combined effect that is therapeutically effective.

As used herein, the term "composition" generally refers to any product comprising the specified ingredients in the specified amounts, as well as any product which results, directly or indirectly, from combinations of the specified ingredients in the specified amounts. It is to be understood that the compositions described herein may be prepared from isolated compounds described herein or from salts, solutions, hydrates, solvates, and other forms of the compounds described herein. It is also to be understood that the compositions may be prepared from various amorphous, non-amorphous, partially crystalline, crystalline, and/or other morphological forms of the compounds described herein. It is also to be understood that the compositions may be prepared from various hydrates and/or solvates of the compounds described herein. Accordingly, such compositions that recite compounds described herein are to be understood to include each of, or any combination of, the various morphological forms and/or solvate or hydrate forms of the compounds described herein.

The terms "fuse", "fused", and the like, as used herein to refer to attachment of one component, composition, molecule, peptide, agent, or another entity to one or more other component, composition, molecule, peptide, agent, or another entity, are to be understood as referring to any kind of attachment known in the art that would provide sufficient stability so that the resulting attached entities can provide the intended function or use. Illustratively, fusing can be via covalent bonding, ionic bonding, or any other suitable attachment known to the skilled artisans.

The term "administering" as used herein includes all means known to those skilled in the medical arts of introducing the compounds and compositions described herein to the patient. It is to be understood that, in the methods described herein, the individual components of a co-administration, or combination, can be administered by any suitable means, contemporaneously, simultaneously, sequentially, separately or in a single pharmaceutical formulation. Where the co-administered compounds or compositions are administered in separate dosage forms, the number of dosages administered per day for each compound may be the same or different. The compounds or compositions may be administered via the same or different routes of administration. The compounds or compositions may be administered according to simultaneous or alternating regimens, at the same or different times during the course of the therapy, concurrently in divided or single forms.

Thus, the Applicants should be understood to claim at least: (i) a PSMA-specific peptide composition as in the Claims, and/or a method for identifying PSMA-specific peptides as in the Claims, and/or a diagnostic composition for cancer imaging comprising a PSMA-specific peptide and an imaging label moiety as in the Claims, and/or a method of use of the diagnostic composition as in the Claims, and/or a ligand for targeted drug delivery to prostate cancer cells as in the Claims, and/or a therapeutic composition for treating cancer comprising a PSMA-specific peptide and a biologically active moiety as in the Claims, and/or a method of use of the therapeutic composition for treating a patient suffering from prostate cancer; (ii) the related methods disclosed and described; (iii) similar equivalent, and even implicit variations of each of these devices and methods; (iv) those alternative embodiments which accomplish each of the functions shown, disclosed, or described; (v) those alternative designs and methods which accomplish each of the functions shown as are implicit to accomplish that which is disclosed and described; (vi) each feature, component, and step shown as separate and independent inventions; (vii) the applications enhanced by the various systems or components disclosed; (viii) the resulting products produced by such systems or components; (ix) methods and apparatuses substantially as described hereinbefore and with reference to any of the accompanying examples; (x) the various combinations and permutations of each of the previous elements disclosed.

The background section of this patent application provides a statement of the field of endeavor to which the invention pertains. This section may also incorporate or contain paraphrasing of certain United States patents, patent applications, publications, or subject matter of the claimed invention useful in relating information, problems, or concerns about the state of technology to which the invention is drawn toward. It is not intended that any United States patent, patent application, publication, statement or other information cited or incorporated herein be interpreted, construed, or deemed to be admitted as prior art with respect to the invention.

The claims set forth in this specification are hereby incorporated by reference as part of this description of the invention, and the applicants expressly reserve the right to use all of or a portion of such incorporated content of such claims as additional description to support any of or all of the claims or any element or component thereof, and the applicants further expressly reserve the right to move any portion of or all of the incorporated content of such claims or any element or component thereof from the description into the claims or vice-versa as necessary to define the matter for which protection is sought by this application or by any subsequent application or continuation, division, or continuation-in-part application thereof, or to obtain any benefit of reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

Additionally, the claims set forth in this specification are further intended to describe the metes and bounds of a limited number of the preferred embodiments of the invention and are not to be construed as the broadest embodiment of the invention or a complete listing of embodiments of the invention that may be claimed. The applicants do not waive any right to develop further claims based upon the description set forth above as a part of any continuation, division, or continuation-in-part, or similar application.

While the disclosure has been illustrated and described in detail in the figures and foregoing description, the same is to be considered as illustrative and not restrictive in character, it being understood that only selected embodiments have been shown and described and that all changes, modifications and equivalents that come within the spirit of the disclosures described heretofore and/or defined by the following claims are desired to be protected. It will be apparent to one of ordinary skill in the art that various changes and modifications can be made to the claimed invention without departing from the spirit and scope thereof. Thus, for example, those skilled in the art will recognize, or be able to ascertain, using no more than routine experimentation, numerous equivalents to the specific substances and procedures described herein. In addition, all publications cited herein are indicative of the level of skill in the art and are hereby incorporated by reference in their entirety as if each had been individually incorporated by reference and fully set forth.

What is claimed is:

1. A peptide consisting of the amino acid sequence of SEQ ID NO: 2.

2. The peptide of claim 1, wherein said peptide specifically binds to the extracellular domain of human PSMA.

3. The peptide of claim 1, wherein said peptide specifically binds to the extracellular domain of human PSMA at the surface of a cell and is internalized by the cell.

4. The peptide of claim 3, wherein said cell is a prostate cancer cell that overexpresses human PSMA.

5. The peptide of claim 1, wherein the peptide shows higher uptake in tumor tissue expressing human PSMA than in other tissues selected from tissues of the liver, kidney, muscle, heart, lung, and spleen.

6. The peptide of claim 5, wherein the uptake ratio in tumor tissue expressing human PSMA relative to muscle tissue is at least 3:1.

7. A composition comprising the peptide of claim 1.

8. A composition comprising the peptide of claim 1 fused to an imaging agent.

9. The composition of claim 8, wherein said imaging agent is a fluorescent agent.

10. The composition of claim 8, wherein said fluorescent agent is fluorescein amidite.

11. A composition comprising the peptide of claim 1 fused to a therapeutic agent.

12. The composition of claim 11, wherein said therapeutic agent is an anti-cancer or chemotherapeutic drug.

* * * * *

SEQUENCE LISTING

```
<160> NUMBER OF SEQ ID NOS: 23

<210> SEQ ID NO 1
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Trp Gln Pro Asp Thr Ala His His Trp Ala Thr Leu
1               5                   10

<210> SEQ ID NO 2
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Thr Ile Gln Pro Tyr Pro Phe Ser Trp Gly Tyr
1               5                   10

<210> SEQ ID NO 3
<211> LENGTH: 12
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 3

Ser Met Ala Gly Glu Gln Ile Ser Trp Ala Leu Ile
1               5                   10

<210> SEQ ID NO 4
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Asn Arg Pro Asp Ser Ala Gln Phe Trp Leu His His
1               5                   10

<210> SEQ ID NO 5
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gln Pro Gly His Ala Ile Leu Ala Gln His Pro Thr
1               5                   10

<210> SEQ ID NO 6
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Tyr Val Asn Ser His Ser Ile Leu Gly Tyr Thr Gly
1               5                   10

<210> SEQ ID NO 7
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Thr Gly His Leu Tyr Pro Thr Arg Met Glu Ile Gln
1               5                   10

<210> SEQ ID NO 8
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

His Ser Asp Asn His Tyr Arg Pro Ala Asp Lys Leu
1               5                   10
```

<210> SEQ ID NO 9
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Tyr Pro Thr Asp Trp Leu Trp His Gly His Asn Lys
1               5                   10

<210> SEQ ID NO 10
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Lys Leu Ala Lys Leu Ala Lys Lys Leu Ala Lys Leu Ala Lys
1               5                   10

<210> SEQ ID NO 11
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
atcagatcta aatcctccaa tgaagc                                          26

<210> SEQ ID NO 12
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
atcaagcttc tgcactgtga aggctgcaac ata                                  33

<210> SEQ ID NO 13
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Ser Gly Tyr Gln Thr Phe Tyr Trp Pro Gly Pro Ile
1               5                   10

<210> SEQ ID NO 14
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

```
Lys Tyr Leu Ala Tyr Pro Asp Ser Val His Ile Trp
 1               5                  10

<210> SEQ ID NO 15
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Val Pro Ser Ile Asp Val Ser Thr Val Ser Tyr Pro
 1               5                  10

<210> SEQ ID NO 16
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Trp Thr Pro Thr Ile Arg Thr Gln Phe Val Pro Ala
 1               5                  10

<210> SEQ ID NO 17
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Ser Ala Arg Leu Ser Met His Glu Met Thr Tyr Leu
 1               5                  10

<210> SEQ ID NO 18
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Asn Phe Thr Leu Met Asn Ala Lys Thr Phe Arg Trp
 1               5                  10

<210> SEQ ID NO 19
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Glu Glu Leu Glu Trp Thr Arg Lys Ala Pro Met Val
 1               5                  10

<210> SEQ ID NO 20
<211> LENGTH: 12
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 20

Thr Asp Asn Thr Met Tyr Asp Lys Gln Phe Gln Lys
1               5                   10

<210> SEQ ID NO 21
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Asn Ala Ser Thr Leu Pro Leu Gln Lys Tyr Pro Thr
1               5                   10

<210> SEQ ID NO 22
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Lys Leu Ser Thr Thr His Asp Arg Leu Met Leu Asn
1               5                   10

<210> SEQ ID NO 23
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Thr Val Pro Gly Asp Ser Ser Pro Pro Arg Leu Asp
1               5                   10
```